US006150416A

United States Patent [19]
Kick et al.

[11] Patent Number: 6,150,416
[45] Date of Patent: Nov. 21, 2000

[54] NANOMOLAR, NON-PEPTIDE INHIBITORS OF CATHEPSIN D

[75] Inventors: Ellen K. Kick, Albany; Jonathan A. Ellman, Oakland; Irwin D. Kuntz, Greenbrae; Christina E. Lee, Berkeley; Guangcheng Liu, Albany; Diana C. Roe, Newark; A. Geoffrey Skillman, San Francisco, all of Calif.

[73] Assignee: The Regents of the University of California, Oakland, Calif.

[21] Appl. No.: 09/018,226

[22] Filed: Feb. 3, 1998

Related U.S. Application Data

[60] Provisional application No. 60/036,903, Feb. 4, 1997.

[51] Int. Cl.[7] .......................... A61K 31/16; A61K 31/36; C07D 317/44; C07D 209/48; C07D 209/02
[52] U.S. Cl. .......................... 514/616; 514/375; 514/414; 514/417; 514/466; 564/158; 549/441; 548/221; 548/454; 548/455; 548/477
[58] Field of Search ..................................... 548/221, 454, 548/455, 477; 549/441; 564/158; 514/375, 414, 417, 466, 616

[56] References Cited

FOREIGN PATENT DOCUMENTS

| 0 159 156 | 10/1985 | European Pat. Off. . |
|---|---|---|
| WO 92/08700 | 5/1992 | WIPO . |

OTHER PUBLICATIONS

Flynn et al., Chemical Library Purification Strategies Based on Principles of Complementary Molecular Reactivity and Molecular Recognition, Journal of the American Chemical Society, vol. 119, No. 21, pp. 4874–4881, May 1997.

Adams, et al., "Novel Inhibitors of the Proteasome and Their Therapeutic Use in Inflammation," *Ann. Rep. Med. Chem.,* 31:279–288 (1996).

Agarwal, et al., "Inhibition of Cathepsin D by Substrate Analogues Containing Statine and by Analogues of Pepstatin," *J. Med. Chem.,* 29:2519–2524 (1986).

Baldwin, et al., "Crystal structures of native and inhibited forms of human cathepsin D: Implications for lysosomal targeting and drug design," *Proc. Natl. Acad. Sci. USA,* 90:6796–6800 (1993).

Edmunds, et al., "Thrombin and Factor Xa Inhibition," *Ann. Rep. Med. Chem.,* 31:51–60 (1996).

Getman, et al., "Discovery of a Novel Class of Potent HIV–1 Protease Inhibitors Containing the (R)–(Hydroxyethyl) urea Isostere," *J. Med. Chem.,* 36:288–291 (1993).

Jupp, et al., "The selectivity of statine–based inhibitors against various human aspartic proteinases," *Biochem. J.,* 265:871–878 (1990).

Kick, et al., "Expedient Method for the Solid–Phase Synthesis of Aspartic Acid Protease Inhibitors Directed toward the Generation of Libraries," *J. Med. Chem.,* 38:1427–1439 (1995).

Kick, et al., "Structure–based design and combinatorial chemistry yield low nanomolar inhibitors of cathepsin D," *Chemistry & Biology,* 4(4):297–307 (1997).

Krafft, et al., "Synthetic Approaches to Continuous Assays of Retroviral Proteases," *Methods in Enzymol.,* 241:70–86 (1994).

Miller, "Regulation of Apoptosis by Members of the ICE Family and the Bcl–2 Family," *Ann. Rep. Med. Chem.,* 31:249–268 (1996).

Westley, et al., "Cathepsin D and Breast Cancer," *Eur. J. Cancer,* 32:15–24 (1996).

Wiley, et al., "Peptidomimetics Derived from Natural Products," *Med. Res. Rev.,* 13:327–384 (1993).

*Primary Examiner*—Mukund J. Shah
*Assistant Examiner*—Brenda Coleman
*Attorney, Agent, or Firm*—Townsend and Townsend and Crew LLP

[57] ABSTRACT

The present invention provides non-peptide cathepsin D binding compounds and methods for using such compounds in the detection, labelling and inhibition of cathepsin D.

35 Claims, 17 Drawing Sheets

Intermediate of Peptide Hydrolysis

Hydroxyethylamine-Based Inhibitors

R₂ substituent

P₁ substituent

A     B     C

D     E     F

G     H     I

J     K     L

R₁ substituent                              R₂ substituent

M     N     O

R₃ substituent

NANOMOLAR, NON-PEPTIDE INHIBITORS OF CATHEPSIN D

This application claims the benefit of U.S. Provisional application Ser. No. 60/036,903, filed Feb. 4, 1997.

GOVERNMENT RIGHTS

This invention was made with Government support under Grant (Contract) Nos. RO1 GM53696 and RO1 GM54051 awarded by the National Institutes of Health. The Government has certain rights in this invention.

FIELD OF THE INVENTION

The present invention relates generally to substances which bind to and inhibit cathepsin D and to the use of these substances in various analytical, diagnostic and therapeutic methods based on this binding capability.

BACKGROUND OF THE INVENTION

A cherished goal of chemists is to design and synthesize compounds with a specific set of properties. This goal is particularly urgent in biological and medicinal chemistry as a part of the drug discovery process. Two powerful new tools in this effort are structure-based design (I. D. Kuntz, *Science* 257, 1078–1082 (1992).; I. D. Kuntz, et al., *Accts. Chem. Res.* 27, 117–123 (1994)) and combinatorial chemistry (L. A. Thompson, et al., *Chem Rev.* 96, 555–600 (1996); E. M. Gordon, et al., *J. Med. Chem.* 37, 1385–1401 (1994)). Structure-based design uses information gleaned from crystallographic and magnetic resonance experiments on a target macromolecule, frequently an enzyme, to guide the selection or design of inhibitors. Computation plays a major role in this endeavor (I. D. Kuntz, et al., *Accts. Chem. Res.* 27, 117–123 (1994); N. C. Cohen, et al., *J. Med. Chem.* 33, 883–894 (1990)). Combinatorial chemistry is based on general chemical transformations that allow different building blocks to be combined in high yield. These transformations can be performed in parallel to synthesize libraries of related compounds rapidly and efficiently (L. A. Thompson, et al., *Chem Rev.* 96, 555–600 (1996); E. M. Gordon, et al., *J. Med. Chem.* 37, 1385–1401 (1994)). Nonetheless, the discovery of a new lead compound or the improvement of the properties of an existing lead are still demanding tasks.

Combinatorial approaches to ligand identification initially focused on biopolymer libraries prepared by either chemical or biological methods (M. A. Gallop, et al., *J. Med. Chem.* 37, 1233–1251 (1994)). For these libraries, all possible combinations of the building blocks are typically used since there are only four natural nucleotide building blocks for aptamer libraries and 20 proteinogenic amino acid building blocks for peptide libraries. Both the structures of the compounds and the theoretical number of compounds in the library are determined by setting the length of the biopolymer chain. Recently, considerable efforts have been directed toward the preparation of libraries of compounds that encompass a wider spectrum of chemical transformations, leading to a broader range of properties than found in peptides or oligonucleotides (L. A. Thompson, et al., *Chem Rev.* 96, 555–600 (1996); E. M. Gordon, et al., *J. Med. Chem.* 37, 1385–1401 (1994)). These new approaches introduce significant challenges into library design.

A crucial element of any library design is the procedure for selecting which compounds to synthesize. This includes the choice of the scaffold, the basic reactions and the nature of the building blocks. If the building blocks are readily available components such as amines, aldehydes or carboxylic acids, the number of potential compounds to be considered can be quite large. For example, combining three building blocks with thousands of components at each position leads to over 1 billion compounds. While different strategies have distinct practical limits, typically a researcher is prepared to synthesize only thousands of spatially separate compounds and tens of millions of compounds in mixtures. Furthermore, evaluation and deconvolution of a very large library become rate-limiting activities (N. K. Terrett, et al., *Bioorg. Med. Chem. Lett.* 5, 917–922 (1995)). Thus, there would be significant advantages to a method of reducing the synthetic effort to a small subset of compounds biased towards the desired properties.

How can the potential choices be efficiently reduced? The standard strategies are diversity selection and directed selection. Diversity approaches attempt to maximize the sampling of chemical and biological properties given a fixed number of compounds (R. J. Simon, et al., *Proc. Natl. Acad. Sci. U.S.A.* 89, 9367–9371 (1992)). In directed libraries the size and often the diversity of the library is reduced by selecting those building blocks that are predicted to have favorable interactions with the target, or by eliminating candidates that are a priori believed to have unfavorable interactions. A directed library can be based on substrate preferences, information about known inhibitors or, on an assessment of the potential interaction of specific functional groups with the target. Both diverse and directed strategies permit a multistage attack with second libraries generated from active compounds found in the first round.

The development of general and efficient approaches to identify small, non-peptidic inhibitors of aspartic proteases continues to be of interest because of their important roles in therapeutically relevant processes (K. Takahashi, Ed., *Aspartic Proteinases Structure, Function, Biology, and Biomedical Implications* (Plenum Press, New York, 1995); J. Adams, et al., *Ann. Rep. Med. Chem.* 31, 279–288 (1996); J. J. Edmunds, et al., *Ann. Rep. Med. Chem.* 31, 51–60 (1996); D. K. Miller, *Ann. Rep. Med. Chem.* 31, 249–268 (1996)). Aspartic acid proteases are a widely distributed family of enzymes that play important roles in fungi, plants, vertebrates and retroviruses. The aspartic acid proteases (characterized by having two aspartic acid residues in the active site) catalyze the hydrolysis of amide bonds with specificity for peptide bonds located between large hydrophobic residues. A number of aspartic acid proteases are important pharmaceutical targets, including renin, cathepsin D, the human immunodeficiency virus (HIV) proteases, human t-cell leukemia virus type 1 (HTLV-1) protease and *candida albicans* aspartic acid protease.

Potent inhibitors of these enzymes can be readily accessed by the incorporation of an isostere that mimics the geometry of the tetrahedral intermediate in place of the scissile bond of the peptide substrate. Unfortunately, these inhibitors have limited therapeutic utility due to the poor oral availability and/or short circulating half-lives that result from their peptidic nature. For this reason, it would be advantageous if structure-based design and combinatorial chemistry techniques could be used to develop non-peptide inhibitors of aspartic acid proteases.

SUMMARY OF THE INVENTION

Cathepsin D is a lysosomal enzyme that plays an important role in protein metabolism (Helseth, et al., *Proc. Natl. Acad. Sci. USA* 81, 3302–3306 (1984)), catabolism (Kay, et al., *Intracellular Protein Catabolism* (eds. Katunuma, et al.), pp. 155–162 (1989)), and antigen processing (Guagliardi, et al., Nature, 343, 133–139 (1990); Van Noort, et al., J. Biol. Chem., 264, 14159–14164 (1989)). The present invention relates to non-peptide cathepsin D-binding compounds and to various uses of these compounds, both therapeutic and diagnostic, based on their cathepsin D-binding properties. These methods include the use of the compounds for detecting and quantitating the presence of cathepsin D in a biological sample for analytical or diagnostic purposes, and the use of the compounds for inhibiting the ability of cathepsin D to process proteins in living cells.

In one embodiment, the present invention provides compounds that are useful as cathepsin D-binding compounds. Such compounds do not incorporate any amino acids and generally have molecular weights of less than about 700–800 daltons. Moreover, these compounds have been found to be potent, non-peptide inhibitors of cathepsin D. Compounds falling within the scope of the present invention have the general structure:

Formula I

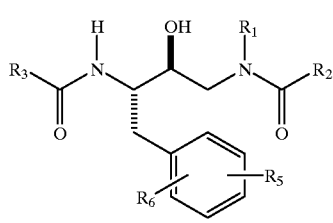

In Formula I, $R_1$, $R_2$ and $R_3$ are members independently selected from the group consisting of alkyl, substituted alkyl, aryl, substituted aryl, arylalkyl, substituted arylalkyl, aryloxyallyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

In Formula I, $R_5$ and R6 are independently selected from the group consisting of hydrogen, halogen, alkyl, substituted alkyl, aryl, substituted aryl, arylalkyl, substituted arylalkyl, aryloxyalkyl and substituted aryloxyalkyl. In an alternative embodiment, $R^5$ and $R^6$ and the carbons to which they are bound, join to form an optionally substituted 9- or 10-ring atom carbocyclic or heterocyclic fused ring system. Typical 9- or 10-atom fused ring systems include, but are not limited to, napthalyl, 1,3-benzodioxolyl, 2,3-benzofuranyl, 1,4-benzodioxanyl, benzimidazoyl, benzothiazolyl etc.

Within the scope of the above Formula I, certain embodiments are preferred. In Formula I, one preferred embodiment is that in which $R_1$ is a functional group including, but not limited to, heteroarylalkyl and substituted arylalkyl. Examples of such functional groups include, but are not limited to, the following:

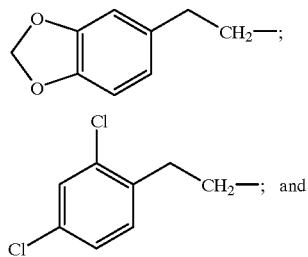

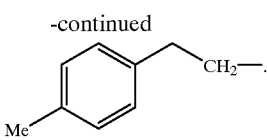

Another preferred embodiment is that in which $R_2$ is a functional group including, but not limited to, heteroarylalkyl, substituted arylalkyl and substituted aryloxyalkyl. Examples of such functional groups include, but are not limited to, the following:

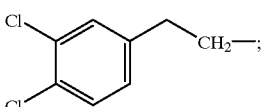

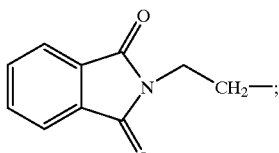

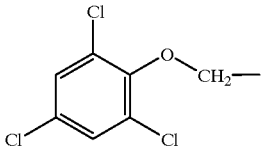

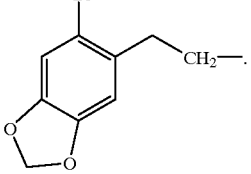

Also preferred is the embodiment in which $R_3$ is a functional group including, but not limited to, substituted aryl, heteroarylalkyl and substituted aryloxyalkyl. Examples of such functional groups include, but are not limited to, the following:

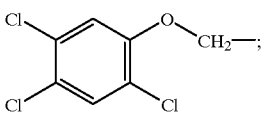

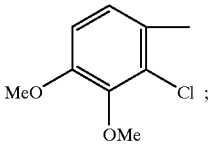

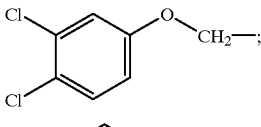

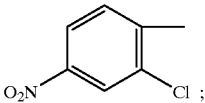

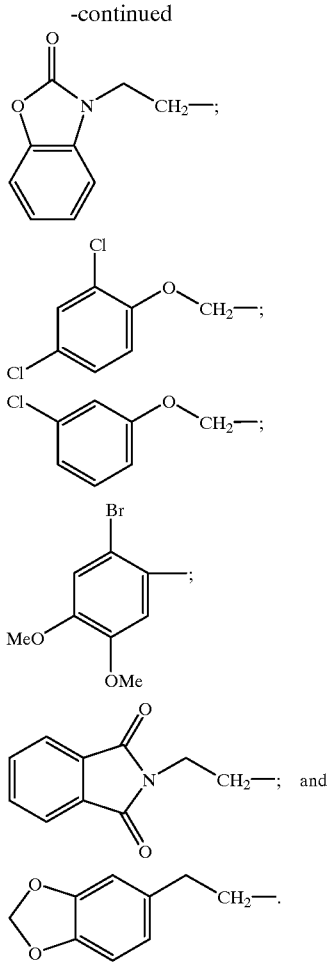

Another preferred embodiment is when $R^5$ and $R^6$ and the carbons to which they are bound join to form an optionally substituted napthalene ring. In other preferred embodiments, $R_5$ and $R_6$ are both hydrogen or $R_5$ is hydrogen and $R_6$ is a meta or para substituent.

By virtue of their ability to bind cathepsin D, the compounds of the present invention are useful for a variety of purposes. For those compounds in which the binding involves the formation of a non-covalent bond, the result is a complex which serves as a labelled form of the protease. The label may be the increase in molecular weight which results from the non-covalent attachment of the cathepsin D-binding compound. Alternatively, the label may be a signal-generating moiety attached to or integrated into the structure of the cathepsin D-binding compound. Examples of such moieties are enzymes, fluorophores, chemophores, high-affinity groups and radioactive (isotopically labeled) atoms. A single complex may contain a single label or multiple labels of either the same or different types. Labelling in accordance with this invention may be performed on cathepsin D proteases regardless of their environment, in vivo or in vitro. Labelling may thus extend to proteases present in tissues and cells. The labelling will generally be followed by an appropriate detection technique, such as autoradiography or any of the wide variety of techniques known to those skilled in the art.

As one application of labelling in accordance with this invention, the cathepsin D-binding compounds of this invention can be used as mechanistic probes of cathepsin D in topologic assays of compounds for which the presence and nature of a cathepsin D binding site is to be determined. A topologic assay, for example, will be performed by combining the following materials in a reaction vessel:

(a) a labelled version of one or more of the compounds of the above formula whose cathepsin D binding site is known, (b) a cathepsin D protease, and (c) a test compound whose cathepsin D binding site is to be determined.

The amount of binding of the first cathepsin D-binding compound to cathepsin D is then determined and compared with the amount of such binding which occurs in the absence of the test compound.

In addition to labelling applications, the cathepsin D-binding compounds can be administered for purposes of inhibiting protein processing by cathepsin D, thereby preventing such proteases from hydrolyzing a peptide substrate. In particular, the inhibition of cathepsin D has a number of important therapeutic applications. Such applications include the treatment of cancer, since elevated levels of cathepsin D in tumors, particularly for breast cancer, have been correlated with poor prognosis due to cathepsin D mediated proteolytic degradation of the extracellular matrix resulting in tumor metastasis. In addition, inhibition of cathepsin D is effective for the treatment of Alzheimer's disease since elevated levels of cathepsin D have been identified in cerebral spinal fluid in Alzheimer's disease patients, and cathepsin D has been shown to have high proteolytic activity against mutant β-protein precursor implicated in Alzheimer's disease. As such, the compounds of the present invention can be used, for example, in the treatment of cancer and Alzheimer's disease.

Other features, objects and advantages of the invention and its preferred embodiments will become apparent from the detailed description which follows.

BRIEF DESCRIPTION OF THE DRAWINGS

FIG. 3A illustrates (a) Modeling the Scaffold. Coordinates and $P_1$–$P_3$ conformations of the pepstatin inhibitor were used as the starting geometry for hydroxyethylamine scaffold. Methyl groups were placed at each of the scaffold's $R_1$–R4 positions. FIG. 3B illustrates (b) Scaffold Conformation. A conformational search about the three torsion angles of the scaffold yielded 4 conformational families. A benzyl sidechain (Bn) was added to each of these families at the $R_4$ position. (c) Evaluating library components. The program BUILDERopt performed a limited conformational search on all possible components at each variable position ($R_1$–$R_3$) on each family, and scored the components by their potential interaction with cathepsin D. The top scoring candidates for each family were merged.

In FIG. 5A, the t-butyl ester of $R_1$=i was used in the coupling reaction. In FIG. 5C, the Boc protected amine of $R_3$=d was used in the coupling reaction. These protecting groups are removed during TFA:$H_2O$ cleavage.

DETAILED DESCRIPTION OF THE INVENTION AND PREFERRED EMBODIMENTS

Figure 1:
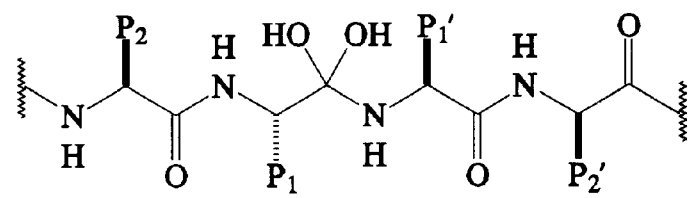
FIG. 1 illustrate isostere-based inhibitor design.
Figure 1:
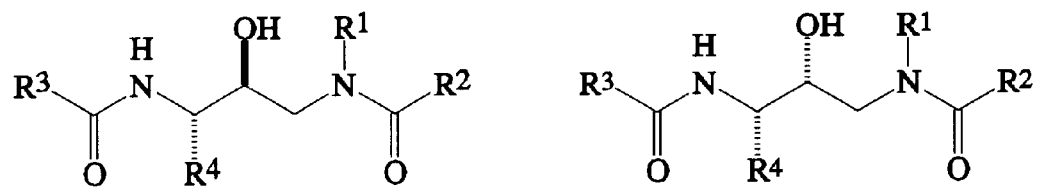

The present invention relates to (i) non-peptide cathepsin D binding compounds; (ii) methods for binding new and known non-peptide compounds to cathepsin D, (iii) methods for using non-peptide cathepsin D-binding compounds to inhibit cathepsin D.

A. Definitions

The term "independently selected" is used herein to indicate that the three R groups, i.e., $R_1$, $R_2$ and $R_3$, can be identical or different (e.g., $R_1$, $R_2$ and $R_3$ may all be substituted alkyls or $R_1$ and $R_2$ may be a substituted alkyl and $R_3$ may be an aryl, etc.).

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term encompasses "substituted alkyls."

"Substituted alkyl" refers to alkyl as just described including one or more functional groups such as lower alkyl, aryl, acyl, halogen (i.e., alkylhalos, e.g., $CF_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl."

The term "arylalkyl" is used herein to refer to a subset of "aryl" in which the aryl group is attached to the nucleus shown in Formula 1 by an alkyl group as defined herein.

"Substituted aryl" refers to aryl as just described including one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached to the nucleus shown in Formula 1 by an alkyl group as defined herein.

The term "acyl" is used to describe a ketone substituent, —C(O)R, where R is alkyl or substituted alkyl, aryl or substituted aryl as defined herein.

The term "halogen" is used herein to refer to fluorine, bromine, chlorine and iodine atoms.

The term "hydroxy" is used herein to refer to the group —OH.

The term "amino" is used to describe primary amines, R—$NH_2$.

The term "alkoxy" is used herein to refer to the —OR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

As used herein, the term "acylamino" describes substituents of the general formula RC(O)NR', wherein R' is a lower alkyl group and R represents the nucleus shown in Formula 1 or an alkyl group, as defined herein, attached to the nucleus.

The term "acyloxy" is used herein to describe an organic radical derived from an organic acid by the removal of the acidic hydrogen. Simple acyloxy groups include, for example, acetoxy, and higher homologues derived from carboxylic acids such as ethanoic, propanoic, butanoic, etc. The acyloxy moiety may be oriented as either a forward or reverse ester (i.e. RC(O)OR' or R'OC(O)R, respectively, wherein R comprises the portion of the ester attached either directly or through an intermediate hydrocarbon chain to the nucleus shown in claim 1).

As used herein, the term "aryloxy" denotes aromatic groups which are linked to the nucleus shown in FIG. 1 directly through an oxygen atom. This term encompasses "substituted aryloxy" moieties in which the aromatic group is substituted as described above for "substituted aryl."

As used herein "aryloxyalkyl" defines aromatic groups attached, through an oxygen atom to an alkyl group, as defined herein. The alkyl group is attached to the nucleus shown in FIG. 1. The term "aryloxyalkyl" encompasses "substituted aryloxyalkyl" moieties in which the aromatic group is substituted as described for "substituted aryl."

As used herein, the term "mercapto" defines moieties of the general structure R—S—R' wherein R and R' are the same or different and are alkyl, aryl or heterocyclic as described herein.

The term "saturated cyclic hydrocarbon" denotes groups such as the cyclopropyl, cyclobutyl, cyclopentyl, etc., and substituted analogues of these structures.

The term "unsaturated cyclic hydrocarbon" is used to describe a monovalent non-aromatic group with at least one double bond, such as cyclopentene, cyclohexene, etc. and substituted analogues thereof.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" defines a subset of "heteroaryl" wherein an alkyl group, as defined herein, links the heteroaryl group to the nucleus shown in FIG. 1.

"Substituted heteroaryl" refers to heteroaryl as just described wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" as described above in which an alkyl group, as defined herein, links the heteroaryl group to the nucleus shown in FIG. 1.

The term "heterocyclic" is used herein to describe a monovalent saturated or unsaturated non-aromatic group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "heterocyclicalkyl" defines a subset of "heterocyclic" wherein an alkyl group, as defined herein, links the heterocyclic group to the nucleus shown in FIG. 1.

The term "optionally substituted napthylene ring" describes a naphthalene ring which may be unsubstituted or may be substituted with one or more functional groups including lower alkyl, halogen, acyl, hydroxy, amino, alkoxy, alkylamino, acylamino, acyloxy or aryl.

The term "substituted heterocyclicalkyl" defines a subset of "heterocyclic alkyl" wherein the heterocyclic nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc.

The term "contacting" is used herein interchangeably with the following: combined with, added to, mixed with, passed over, incubated with, flowed over, etc. Moreover, the cathepsin D binding compounds of present invention can be "administered" by any conventional method such as, for example, parenteral, oral, topical and inhalation routes as described herein.

"An amount sufficient" or "an effective amount" is that amount of a given cathepsin D compound which exhibits the binding/inhibitory activity of interest or, which provides either a subjective relief of a symptom(s) or an objectively identifiable improvement as noted by the clinician or other qualified observer.

B. Non-peptide Protease Binding Compounds

Figure 2:
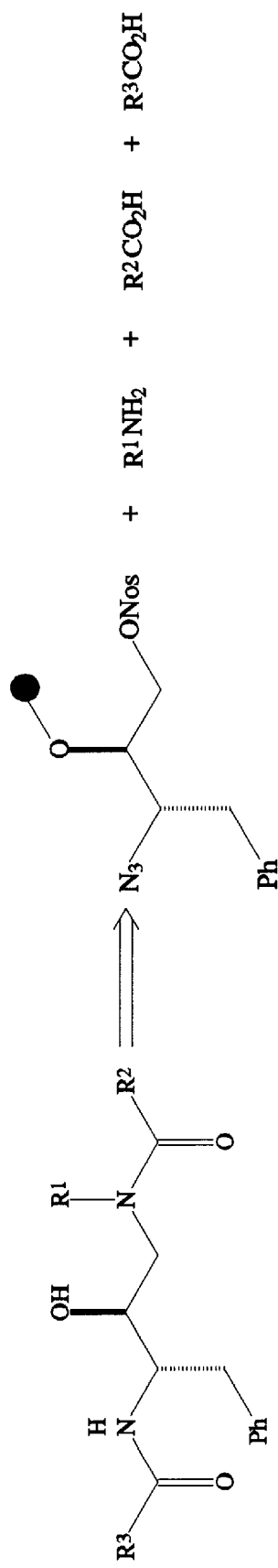
FIG. 2 illustrates components employed to prepare the libraries targeting cathepsin D. The same disconnections provide scaffold 2. Isocyanates and sulfonyl chlorides, which can be used to incorporate $R_2$ and $R_3$, provide ureas and sulfonamides, respectively.

The present invention relates to the identification of a number of small-molecule compounds which are capable of binding to and inhibiting cathepsin D employing a combined combinatorial library (see, e.g., Thompson, et al., *Chemical Reviews*, 96, 555–600 (1996)) and structure based design approach (see, e.g., Kuntz, I.D., *Science*, 257, 1078–1082 (1992)). The libraries of potential cathepsin D binding compounds were based upon the display of functionality about the hydroxyethylamine scaffold illustrated in FIG. 1. For the initial libraries, the $P_1$ sidechain ($R^4$) was held constant as a benzyl substituent based upon X-ray crystallographic data of cathepsin D complexed with the peptide-based natural product pepstatin as reported by Erickson (Baldwin, et al., *Proc. Natl. Acad. Sci. USA*, 90, 6796–6800 (1993)). As illustrated in FIG. 2, diversity was introduced at three positions: a primary amine introduced the $R_1$ substituent, and acylating agents serve to introduce the $R_2$ and $R_3$ substituents. Once prepared, the libraries were screened to identify compounds capable of binding to and inhibiting cathepsin D. Thereafter, a second generation library was prepared in an effort to further explore variants of the most active compounds. Thus, by combining a structure-based design and a combinatorial library approach, non-peptidic compounds capable of binding to and inhibiting cathepsin D have now been identified.

Accordingly, in one embodiment, the present invention provides compounds having the general formula:

Formula I

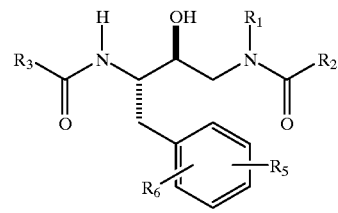

In Formula I, $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

In Formula I, $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl. In an alternative embodiment, $R^5$ and $R^6$ and the carbons to which they are bound, join to form an optionally substituted 9- or 10-ring atom carbocyclic or heterocyclic fused ring system. Typical 9- or 10-atom ring systems include, but are not limited to, napthalyl, 1,3-benzodioxolyl, 2,3-benzofuranyl, 1,4-benzodioxanyl, benzimidazoyl, benzothiazolyl etc.

Within the scope of the above Formula I, certain embodiments are preferred. In Formula I, one preferred embodiment is that in which $R_1$ is a functional group including, but not limited to, heteroarylalkyl and substituted arylalkyl. Examples of such functional groups include, but are not limited to, the following:

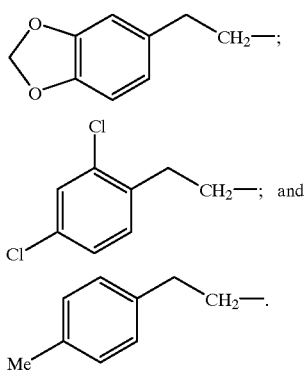

Another preferred embodiment is that in which $R_2$ is a functional group including, but not limited to, heteroarylalkyl, substituted arylalkyl and aryloxyalkyl. Examples of such functional groups include, but are not limited to, the following:

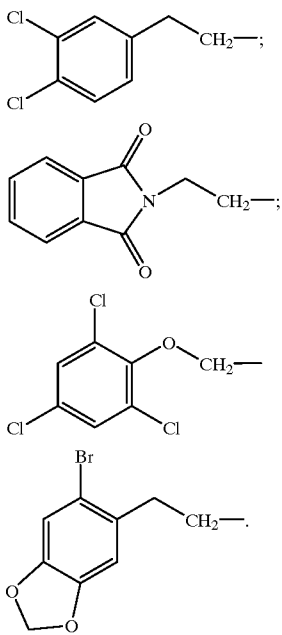

Also preferred is the embodiment in which $R_3$ is a functional group including, but not limited to, substituted aryl, heteroarylalkyl and substituted aryloxyalkyl. Examples of such functional groups include, but are not limited to, the following:

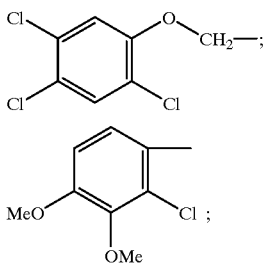

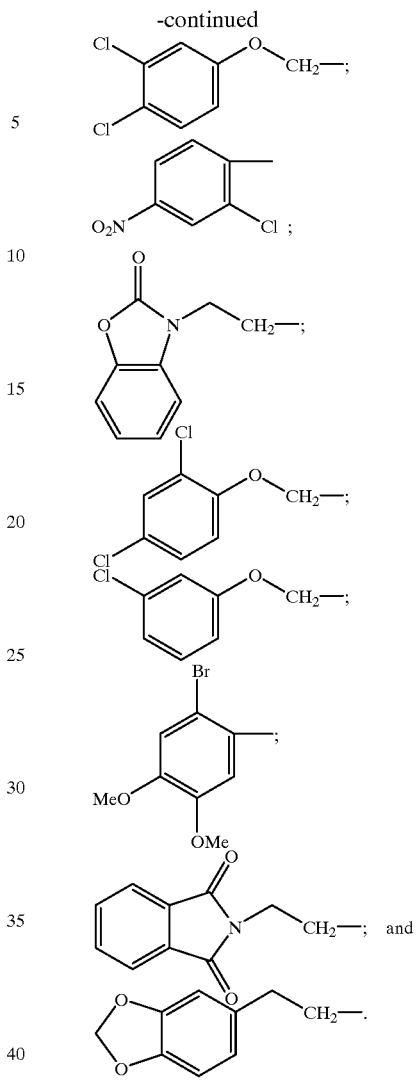

Another preferred embodiment is when $R^5$ and $R^6$ and the carbons to which they are bound, join to form an optionally substituted napthalene ring. In other preferred embodiments, $R_5$ and $R_6$ are both hydrogen, or $R_5$ is hydrogen and $R_6$ is a meta or para substituent on the benzyl ring.

In Formula I, the benzyl ring may be replaced by the substituent $R_4$ (see below). In this embodiment, $R_4$ can be a member selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl.

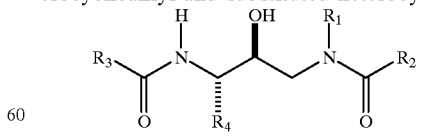

Table 1 sets forth compounds in accordance with the present invention which are particularly preferred. The compounds in this table and throughout this specification are referred to by code numbers, which are used for convenience only, and are strictly arbitrary for purposes of this invention.

TABLE 1

Exemplar Protease Binding Compounds

| Compound Code No. | Protease Binding Compounds Formula |
|---|---|
| EAA | |
| EFA | |
| EHA | |

TABLE 1-continued
Exemplar Protease Binding Compounds
| Compound Code No. | Protease Binding Compounds Formula |
|---|---|
| FAA | 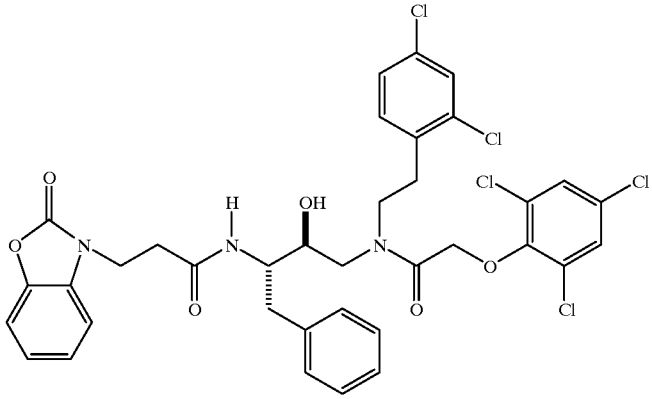 |
| FFA | 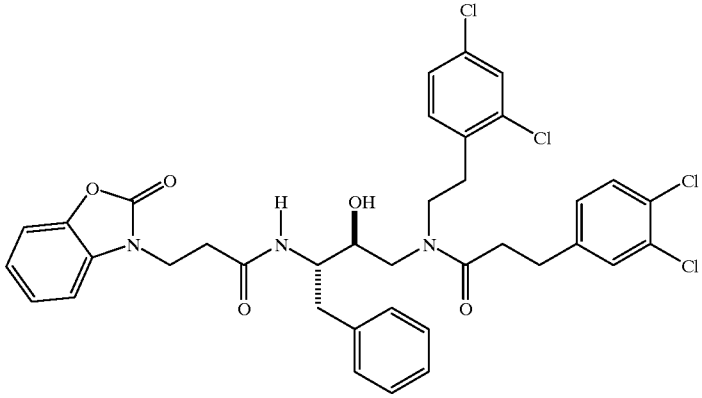 |
| FHA | 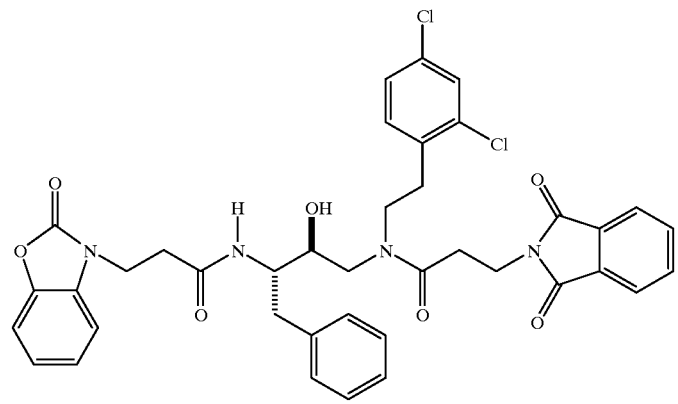 |

TABLE 1-continued

Exemplar Protease Binding Compounds

| Compound Code No. | Protease Binding Compounds Formula |
|---|---|
| EHB | |
| EFD | |
| EHD | |

TABLE 1-continued
Exemplar Protease Binding Compounds
| Compound Code No. | Protease Binding Compounds Formula |
|---|---|
| EEF | 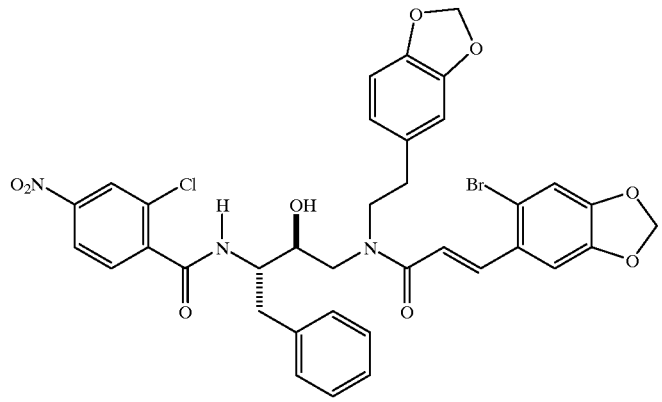 |
| EHF | 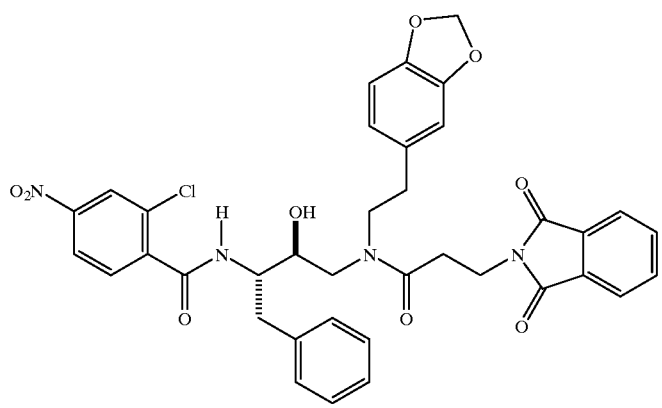 |
| FHF | 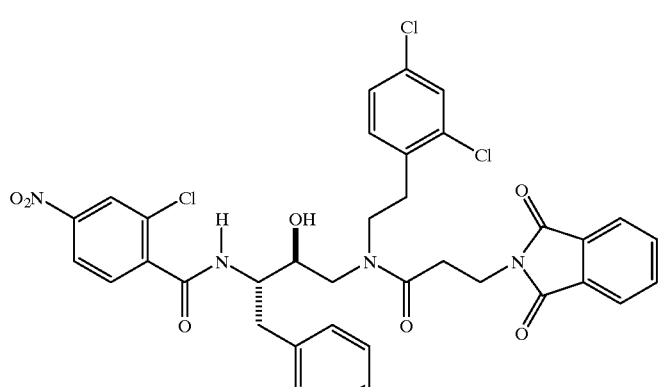 |

TABLE 1-continued

Exemplar Protease Binding Compounds

| Compound Code No. | Protease Binding Compounds Formula |
|---|---|
| EFH | |
| EHH | |
| FFH | |

TABLE 1-continued

Exemplar Protease Binding Compounds

| Compound Code No. | Protease Binding Compounds Formula |
|---|---|
| FAH | |
| EFI | |
| EHI | |

TABLE 1-continued

Exemplar Protease Binding Compounds

| Compound Code No. | Protease Binding Compounds Formula |
|---|---|
| EAJ | (structure) |
| EFJ | (structure) |
| EGJ | (structure) |

TABLE 1-continued

Exemplar Protease Binding Compounds

| Compound Code No. | Protease Binding Compounds Formula |
|---|---|
| EHJ | |
| FHJ | |
| EHO | |

TABLE 1-continued
Exemplar Protease Binding Compounds
| Compound Code No. | Protease Binding Compounds Formula |
|---|---|
| FHO | 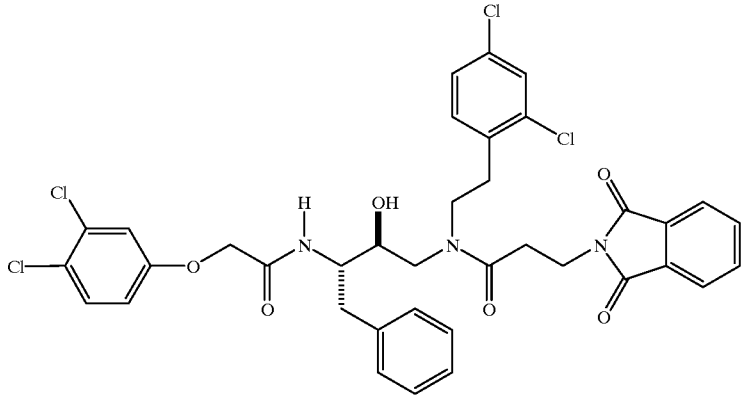 |
| EHM | 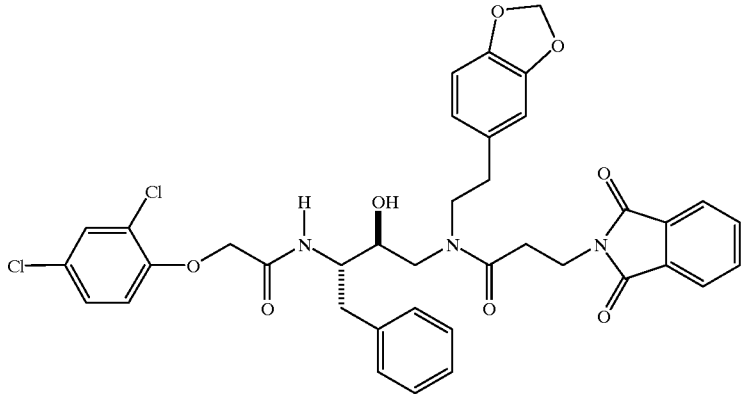 |
| EHR | 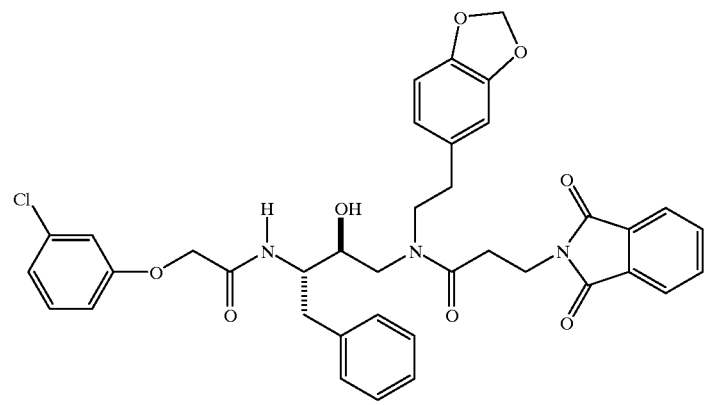 |

TABLE 1-continued

Exemplar Protease Binding Compounds

| Compound Code No. | Protease Binding Compounds Formula |
|---|---|
| EHS | (structure) |
| UHD | (structure) |

The compounds of the present invention can be synthesized in a variety of ways, using conventional synthetic chemistry techniques. Typically, the compounds of the present invention are prepared according to the reaction scheme set forth in FIG. 2, wherein $R_1$, $R_2$ and $R_3$ are as defined above. The use of appropriate organic solvents, temperature and time conditions for running the reactions are within the level of skill in the art. Reactions of this type are generally described by E. K. Kick and J. A. Ellman, *J. Med. Chem.* 38, 1427–1430 (1995), the teachings of which are hereby incorporated by reference.

C. Binding Methods

In one embodiment, the present invention contemplates using the above-named compounds to label cathepsin D. In one case, cathepsin D can be "labelled" by virtue of an increase in molecular weight due to non-covalent binding of the compound. The increase in molecular weight can be detected by any sizing technique, such as HPLC, SDS-PAGE, and mass spectroscopy.

The present invention also contemplates labelling methods which involve attaching to the compounds or integrating into their structure at least one moiety capable of being detected, either by signal emission or by specific binding. Moieties such as these are generally intended to facilitate the detection of cathepsin D or of molecules bound to cathepsin D. Examples of types of moieties useful for this purpose are enzymes, fluorophores, high-affinity conjugates, chemophores and radioactive atoms (radioisotopes). Examples of enzymes are alkaline phosphatase, β-galactosidase and glucose oxidase. An example of an affinity conjugate system is the biotin-avidin system. An example of a fluorophore is fluorescein. An example of a chemophore is luminol. Examples of radiolabels are $^3$H, $^{14}$C, $^{231}$I and $^{125}$I. Other detection moieties known to and used by those of skill in the art can be used in the methods of the present invention.

As indicated above, single or multiple labels can be present in a single complex, with multiple labels being the same or different. In the use of the invention for facilitating the detection of cathepsin D, preferred labels are tritium ($^3$H) and $^{14}$C. A preferred label for facilitating the detection of molecules bound to the compounds is biotin.

The present invention contemplates using labelled analogs of the compounds disclosed herein to label cathepsin D in tissues and cells. This type of labelling can be used both diagnostically and prognostically. Quantitation of cathepsin by this labelling technique can be performed in many ways known to the art, including methods using tritiated analogs of the compounds and autoradiography of treated cells on microscope slides. In addition, there are a number of automated detection systems described for fluorescent staining that also can be employed. See, for example, Resnick, et al., U.S. Pat. Nos. 4,125,828 and 4,207,554, hereby incorporated herein by reference.

The present invention also contemplates the in vitro use of the compounds disclosed herein as topologic and mechanistic probes of cathepsin D. In one embodiment, the topologic assay utilizes labelled compounds whose protease binding sites are known. In addition, the known cathepsin D-binding sites of the compounds of the invention allow the compounds to be used in the determination of binding sites for other (peptide and non-peptide) compounds. In one embodiment, a compound of this invention is used in a competition assay with a second compound whose protease binding site is to be tested. The compounds of this invention can be added to cathepsin D together or in any sequential order. Where the compound of this invention is labelled, it is preferred that the second compound be added first to allow it to block (if possible) the binding site. Similarly, where the second compound is labelled, it is preferred that the compound of this invention be added first.

The present invention also contemplates binding methods to immobilize cathepsin D. In one embodiment, the present invention contemplates using a cathepsin D-binding compound of the invention that will bind non-covalently to cathepsin D to immobilize this protease on a solid support. Such a method is useful in the purification of the protease.

Binding of the above-described compounds is in part a function of solubility. If needed, the solubility of these compounds can be enhanced in aqueous solutions by the use of a co-solvent. The preferred co-solvent is dimethylsulfoxide (DMSO). The concentration range of DMSO is between 0.1% and 10%, with a preferred range of between 0.5% and 5%.

D. Cathepsin D Inhibition

The compounds of the present invention have been found to be potent inhibitors of cathepsin D. As such, the present invention contemplates using the compounds of the present invention to inhibit cathepsin D, either in vivo or in vitro. In one embodiment, the present invention provides a method of inhibiting cathepsin D, the method comprising contacting cathepsin D with a compound of the formula:

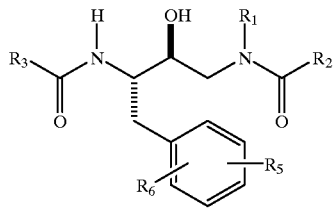

Formula I

In the above formula, $R_1$, $R_2$ and $R_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl. The prior discussions pertaining to $R_1$, $R_2$ and $R_3$ and their preferred embodiments are fully applicable to the cathepsin D inhibitors used in this method of the present invention and, thus, will not be repeated with respect to this particular method. $R_5$ and $R_6$ are as defined above.

In another embodiment, the present invention provides a method of inhibiting protein processing by cathepsin D in living cells, the method comprising contacting the cells with an effective amount of a compound of the formula

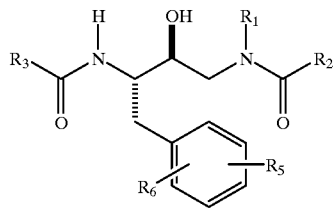

Formula I

The prior discussions pertaining to $R_1$, $R_2$ $R_3$ $R_5$ and $R_6$ and their preferred embodiments are fully applicable to the cathepsin D inhibitors used in this method of the present invention and, thus, will not be repeated with respect to this particular method.

Compounds capable of inhibiting cathepsin D can readily be identified using the assays described herein which measure a change in the hydrolysis of a peptide substrate. More particularly, a fluorometric high through-put assay for activity toward human liver cathepsin D (Calbiochem) can be used to screen the compounds of the present invention for their ability to inhibit cathepsin D. This assay was previously described by G. A. Kraft, et al., Methods Enzymol. 241, 70–86 (1994), the teachings of which are incorporated herein by reference. Moreover, the peptide substrate (Ac-Glu-Glu(Edans)-Lys-Pro-Ile-Cys-Phe-Phe-Arg-Leu-Gly-Lys(Methyl Red)-Glu-$NH_2$) used in the assay has been previously reported ($K_6$=6 $\mu$M) (E. T. Baldwin, et al., Proc. Natl. Acad. Sci., U.S.A. 90, 6796–6800 (1993)). Generally, the reactants are mixed, the reaction is allowed to proceed for a specific period of time and the fluorescence of the reaction products is monitored to determine the extent to which the peptide substrate has been cleaved. Compounds found to exhibit inhibitory activity towards cathepsin D using the foregoing assay can be synthesized on a larger scale and a more detailed kinetic analaysis can be carried out using an assay similar to that set forth in Table 3, infra, and described in greater detail by G. A. Kraft, et al., Methods Enzymol. 241, 70–86 (1994). As such, following the methods of the present invention, compounds can be readily synthesized and screened to identify compounds that inhibit cathepsin D.

As explained above, cathepsin D is a lysosomal enzyme that plays an important role in protein metabolism, catabolism and antigen processing. As a result of their ability to inhibit cathepsin D, the compounds of the present invention can be used for a number of therapeutic applications. Such applications include the treatment of cancer, since elevated levels of cathepsin D in tumors, particularly for breast cancer, have been correlated with poor prognosis due to cathepsin D mediated proteolytic degradation of the extracellular matrix resulting in tumor metastasis (see, e.g., B. R. Westley, et al., Eur. J. Cancer 32, 15–24 (1996)).

As such, the present invention provides a method for inhibiting the growth of a tumor cell, the method comprising contacting the tumor cell with a compound having the formula:

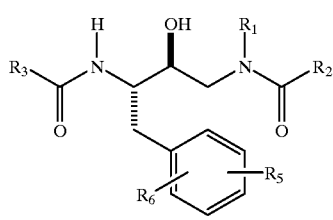

Formula I

The prior discussions pertaining to $R_1$, $R_2$, $R_3$ $R_5$ and R6 and their preferred embodiments are fully applicable to the cathepsin D inhibitors used in this method of the present invention and, thus, will not be repeated with respect to this particular method.

In a presently preferred embodiment, the compounds of the present invention are used to inhibit the growth of a tumor cell in a mammalian subject, the method comprising administering to the mammalian subject a therapeutically effective amount of a compound of the present invention. In accordance with this method, mammalian subjects include, but are not limited to, humans, laboratory animals, domestic pets and farm animals. Moreover, tumor cells include, but are not limited to, lung, colon, breast, ovarian, prostate and hepatic tumor cells. In a presently preferred embodiment, the tumor cells are breast tumor cells.

In addition to the foregoing, inhibition of cathepsin D is effective for the treatment of Alzheimer's disease since elevated levels of cathepsin D have been identified in cerebral spinal fluid in Alzheimer's disease patients, and cathepsin D has been shown to have high proteolytic activity against mutant β-protein precursor implicated in Alzheimer's disease (see, e.g., Ladror, U. S., et al., *J. Biol. Chem.* 269, 18422–18428 (1994); Cataldo, A. M., et al., *J. Neurosci.* 16, 186–199 (1996)).

As such, the present invention provides a method of inhibiting the proteolysis of a mutant β-protein precursor in a patient afflicted with Alzheimer's disease, the method comprising administering to the patient a cathepsin D inhibitor in an amount effective to inhibit the proteolysis of the mutant β-protein precursor and a pharmaceutically acceptable carrier, the cathepsin D inhibitor having the formula:

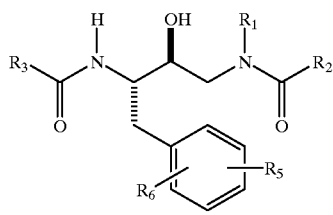

Formula I

The prior discussions pertaining to $R_1$, $R_2$, $R_3$ $R_5$ and $R_6$ and their preferred embodiments are fully applicable to the cathepsin D inhibitors used in this method of the present invention and, thus, will not be repeated with respect to this particular method.

The compounds, i.e., aspartic protease inhibitors, of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Linger, *Science* 249:1527–1533 (1990), which is incorporated herein by reference.

The compounds of the present invention can be administered alone, in combination with each other, or they can be used in combination with other known compounds (e.g., other protease inhibitors). In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting. It should be noted that since the compounds of the present invention are non-peptidic in nature, they tend to have better pharmacokinetic properties (e.g., better oral availability and increased circulating half-lives) than compounds that are peptidic in nature.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Preferred formulations of the compounds are oral preparations, particularly capsules or tablets containing each from about 10 milligrams up to about 1000 milligrams of active ingredient. The compounds are formulated in a variety of physiologically compatible matrixes or solvents suitable for ingestion or injection.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

A. Specific Approach

One powerful strategy to target an enzyme class is to incorporate a stable mimetic or isostere of the transition state or of an intermediate of the enzyme-catalyzed reaction (R. A. Wiley, et al., *Med. Res. Rev.* 13, 327–384 (1993)). The libraries for potential cathepsin D inhibitors are based upon the well-known hydroxyethylamine isostere (see, FIG. 1). For the initial libraries, the $P_1$ side chain ($R_4$) is held constant as the benzyl substituent, based on the X-ray crystallographic structure of cathepsin D complexed with the natural peptide inhibitor pepstatin (E. T. Baldwin, et al., *Proc. Natl. Acad. Sci., U.S.A.* 90, 6796–6800 (1993)), and upon inhibition constants of peptide-based inhibitors (R. A. Jupp, et al., *Biochem. J.* 265, 871–878 (1990); N. S. Agarwal, etc., *J. Med. Chem.* 29, 2519–2524 (1986)).

In a pilot study both S and R epimers at the hydroxyl carbon (see, structures 1 and 2 of FIG. 1) were prepared since both diastereomers have been found in potent inhibitors of other aspartic acid proteases (R. A. Wiley, et al., *Med. Res. Rev.* 13, 327–384 (1993)). Because inhibition at 1 $\mu$M was only found with compounds of scaffold 1 in the pilot study, further syntheses of libraries toward cathepsin D used only scaffold 1. Computer modeling (see below) predicted that structure 1 (FIG. 1) would provide the most potent inhibitors. Diversity is introduced in three positions: a primary amine for the $R_1$ substituent and acylating agents for the $R_2$ and $R_3$ substituents (FIG. 2). The optimization of the synthesis sequence was previously reported (E. K. Kick, J. A. Ellman, *J. Med. Chem.* 38, 1427–1430 (1995)).

The library synthesis was designed to use commercially available compounds for incorporation of the functionality at $R_1$, $R_2$, and $R_3$. Exhaustive combination of available materials would provide a library of over 10 billion compounds. To reduce these possibilities in a sensible way, version 93.2 of the Available Chemical Directory (ACD) from MDL Information Systems (San Leandro, Calif.) was used to search for all amines, carboxylic acids, sulfonyl chlorides and isocyanates with MW<275 daltons. Compounds with functionality obviously incompatible with the synthesis were eliminated. The resulting list included approximately 700 amines and 1900 acylating agents. However, this list still provided access to more than 1 billion compounds. Clearly, additional selection criteria were required, and a computational screening process was turned to in an effort to enhance selection.

B. Directed Library Design

Figure 3A:
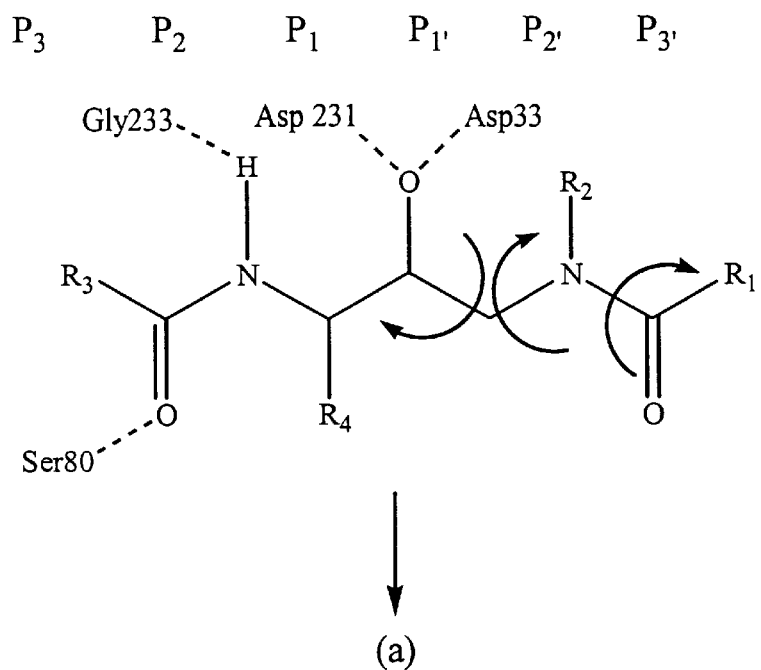
FIGS. 3A–3B illustrate the used of BUILDERopt in designing the combinatorial library.
Figure 3B:
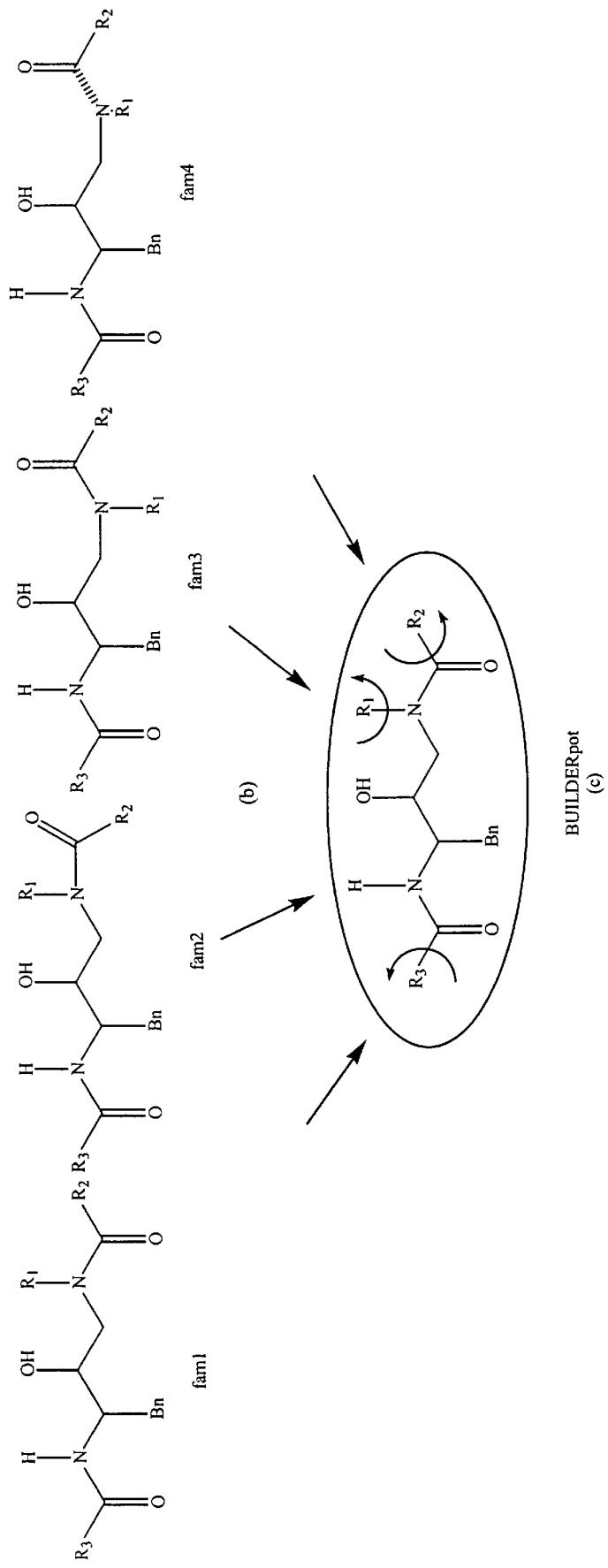

The structure-based design process began with coordinates for pepstatin in a complex with cathepsin D (E. T. Baldwin, et al., *Proc. Natl. Acad. Sci., U.S.A.* 90, 6796–6800 (1993)). The scaffold is identical to pepstatin on the $P_1$–$P_3$ side, but differs on the $B_1$–$P_3$, side and cannot form the same hydrogen bonds with the enzyme (FIG. 3A). Thus, the pepstatin positions for the $P_1$–$P_3$ side were used and the three scaffold torsion angles on the $P_1$–$P_3$ side were systemically rotated. Each rotation was followed by energy minimization within the cathepsin D active site, using the AMBER (S. J. Weiner, et al., *J. Am. Chem. Soc.* 106, 765–784 (1984)) force field in Sybyl, a molecular modeling software package from Tripos Associates (St. Louis, Mo.). During minimization, the enzyme was kept rigid, but full flexibility of the scaffold was allowed. Both S and R epimers, structures 1 and 2, were modeled using methyl groups for each of the $R_1$–$R_4$ groups. The conformational energies of the R epimers were generally ca. 2 kcal higher than for S epimers, leading to the prediction that the S epimers would bind more tightly than the R epimers. All minimized conformations of S epimers within a 2 kcal/mol range were collected and clustered into four families based on geometric similarity (FIG. 3B). A benzyl group was added to each family at the $R_4$ position. The processed list of compounds for the ACD was passed through Sybyl to obtain Gasteiger and Marsili partial atomic charges for each component (J. Gasteiger, et al., *Tetrahedron Lett* 36, 3219 (1980); J. Gasteiger, M. Marsili, Organ. Magn. Reson. 15, 353 (1981)). To reduce the computational time for searching the components, compounds with more than 4 torsional bonds were identified and removed. A new feature of the BUILDER molecular modeling program (R. A. Lewis, et al., *J. Mol. Graphics* 10, 66–78 (1992); D. C. Roe, and Kuntz, I. D., *JCAMD* 9, 269–282 (1995)), called BUILDERopt (D. C. Roe, Dissertation, University of California, San Francisco (1995)), was used to position each of the $R_1$, $R_2$, and $R_3$ components onto the scaffold and to perform a full conformational search for the torsion angles of the substituent at 15 degree increments. In order to reduce the combinatoric problem, the $R_1$, $R_2$, and $R_3$ components were examined independently, but a probability-based clash grid was constructed to identify $R_1$ and $R_2$ conformations that might overlap. For example, if an $R_1$ conformation clashed with more than 50% of the $R_2$ components, that conformation was discarded. Each rotation was then examined for intramolecular clashes with the scaffold and overlap with cathepsin D. Each accepted conformation was rigid-body minimized (D. A. Gschwend, et al., *J. Compt-Aided Drug Design* 10, 123–132 (1996)) and scored with a force-field grid (E. C. Meng, et al., *J. Comput. Chem.* 13, 505–524 (1992)). The total computer time required to evaluate all torsion angles for all sidechains attached to four different scaffold conformations was 16 hours on a Silicon Graphics Iris R4400. The fifty best scoring components for all families were merged for each of the three variable positions, and sorted by overall lowest score. Components with cost above $35/gm were removed, leaving 34, 35, and 41 components at $R_1$, $R_2$ and $R_3$, respectively. Each remaining component was structurally fingerprinted (Daylight Clustering Toolkit, Daylight Chemical Information Systems, Inc., Santa Fe, N.M.) and hierarchically clustered (similarity cutoff=0.63) (H. C. Romesburg, *Cluster Analysis For Researchers* (Lifetime Learning Publications, Belmont, Calif., 1984)) using the Tanimoto similarity metric (P. Willett, *Similarity and Clustering in Chemical Information Systems* (John Wiley & Sons, New York, N.Y., 1987); P. Willett, et al., *J. Chem. If. Comput. Sci.* 26, 109–118 (1986)). For $R_1$, $R_2$, and $R_3$, the ten best scoring components from unique clusters were selected for the directed library.

C. Diverse Library Design

A diverse library, which was set at the same size as the directed library, was prepared to provide a "hit" rate when structure-based methods were not employed. The diverse library was designed to maximize the variety of functional groups and structural motifs of the library components. The sidechains for this library were selected by clustering the original list of components based on their similarity to each other. Components were clustered with the Jarvis-Patrick algorithm (R. A. Jarvis, et al., *IEEE Comput* C22, 1025–1034 (1973)) using the Daylight connectivity measure of similarity (Daylight Clustering Toolkit, Daylight Chemical Information Systems, Inc., Santa Fe, N.M.) and a binary Tanimoto metric (P. Willett, *Similarity and Clustering in Chemical Infonnation Systems* (John Wiley & Sons, New York, N.Y., 1987); P. Willett, et al., *J. Chem. If Comput. Sci.* 26, 109–118 (1986)). In the Jarvis-Patrick method, two compounds are placed in the same cluster if they: 1) are neighbors of one another, and 2) share at least p neighbors from a list of q nearest neighbors, where p and q are adjustable parameters. The compound nearest the cluster centroid was chosen as the cluster representative.

The $R_1$ (amine) components were clustered directly as the primary amines. The $R_2$ and $R_3$ acylating agents were each attached to a portion of the scaffold before clustering to yield the proper chemical context at the linkage site. The first round of clustering yielded 47, 154, and 162 clusters using p/q=4/11, p/q =4/12, and p/q=4/12 for $R_1$, $R_2$, and $R_3$, respectively. The representative $R_2$ and $R_3$ components were clustered a second time (p/q=4/7 for $R_2$ and p/q =4/7 for $R_3$), resulting in 23 $R_2$ and 35 $R_3$ components. It is noted that it is not practical to condense a large number of compounds into an arbitrarily small number of clusters because the cluster membership can become very diverse. Final selection of ten compounds from each list was based upon: size, cost, availability and synthetic feasibility. Additionally, a balance of functional groups for each set of sidechains was sought. A comparison of the directed and diverse libraries (FIGS. 4 and 5) shows the much greater range of functionality spanned in the diverse library.

D. Library Synthesis and Screening

Figure 4A:
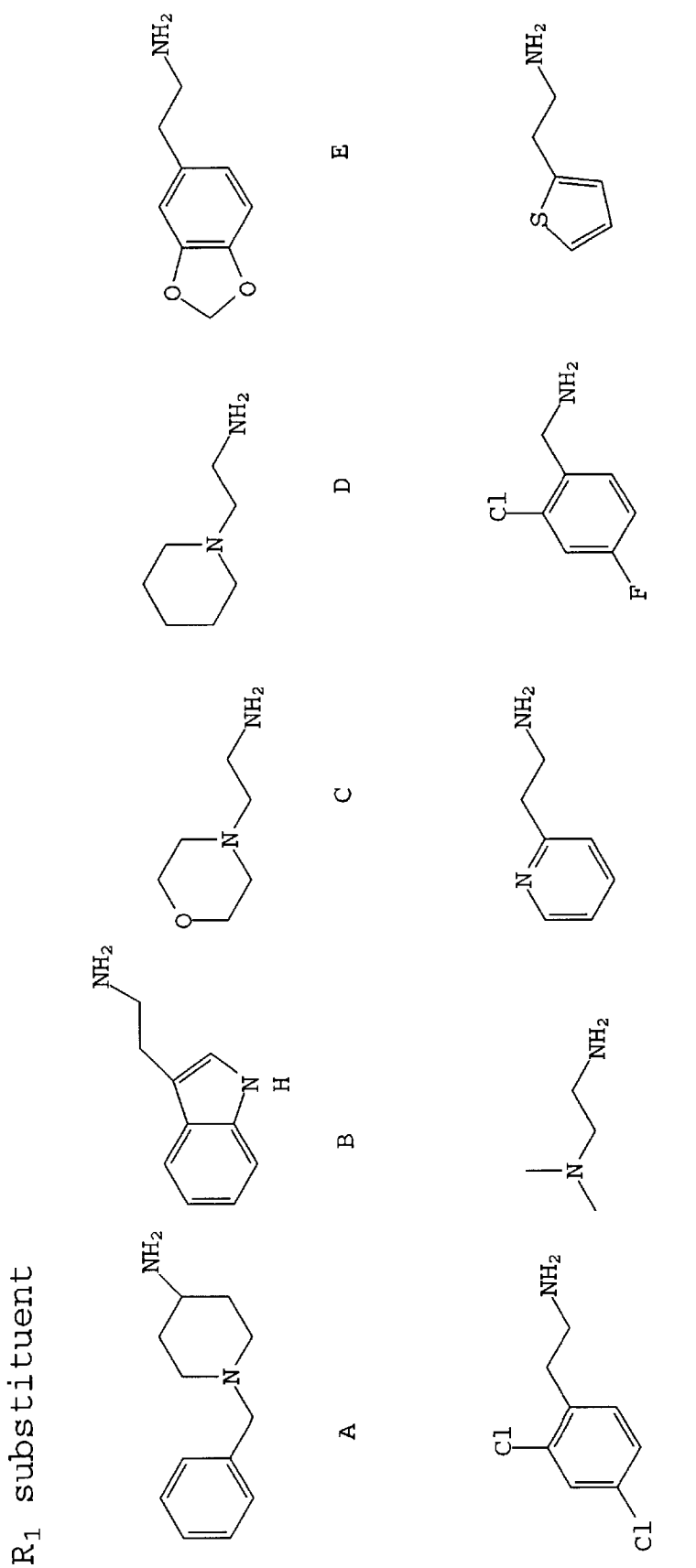
FIGS. 4A–4C illustrate the components used to prepare the Directed Library. Directed library components are labeled with a letter code. EHA is defined as $R_1$=E; $R_2$=H; and $R_3$=A.
Figure 4B:
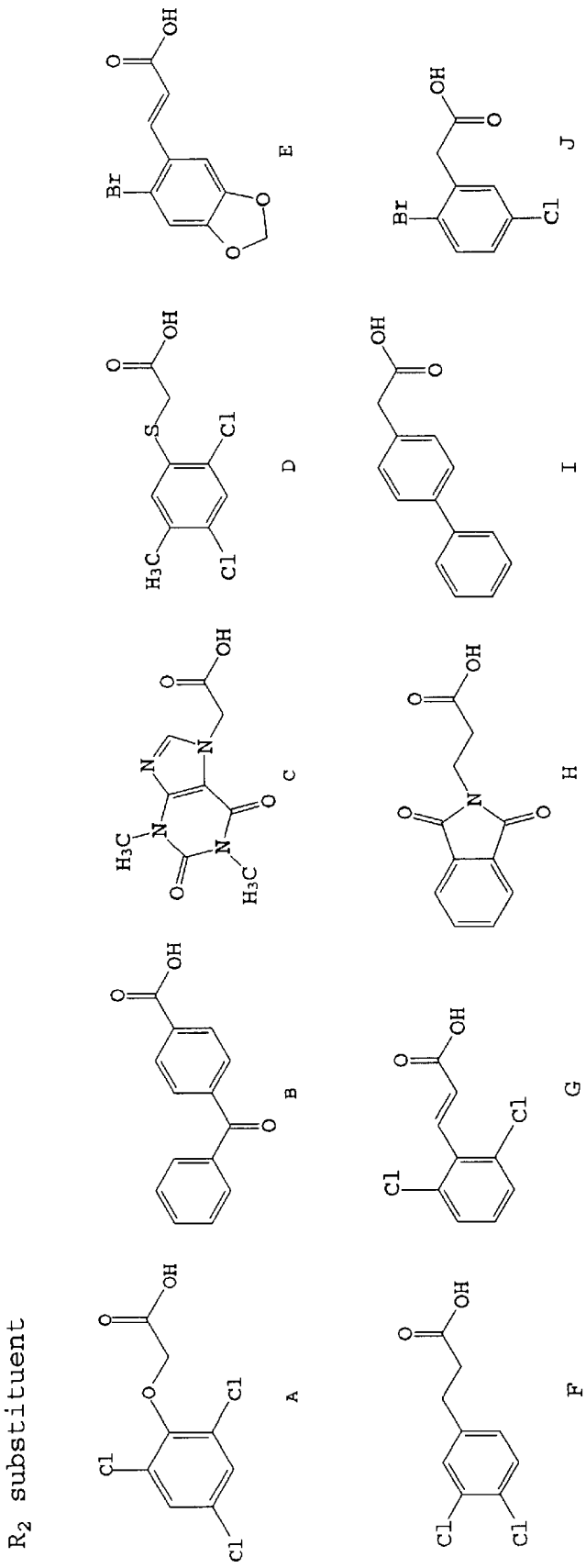
Figure 4C:
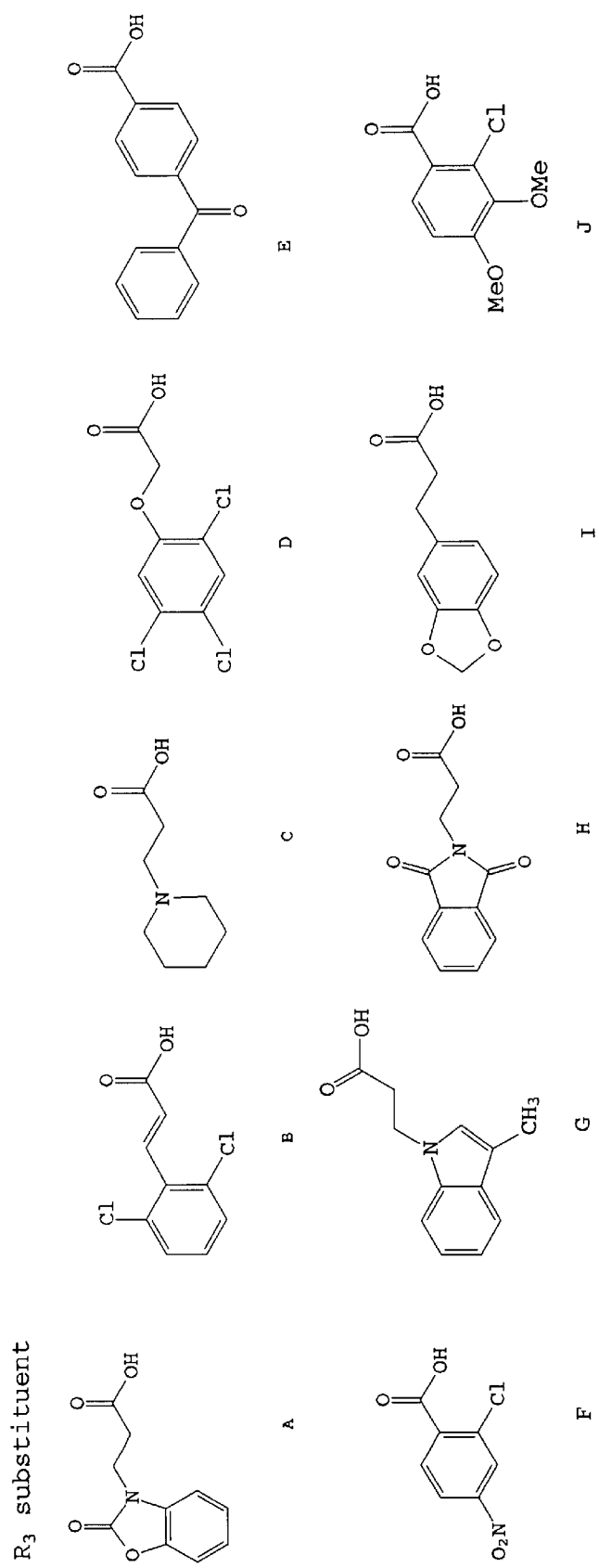
Figure 5A:
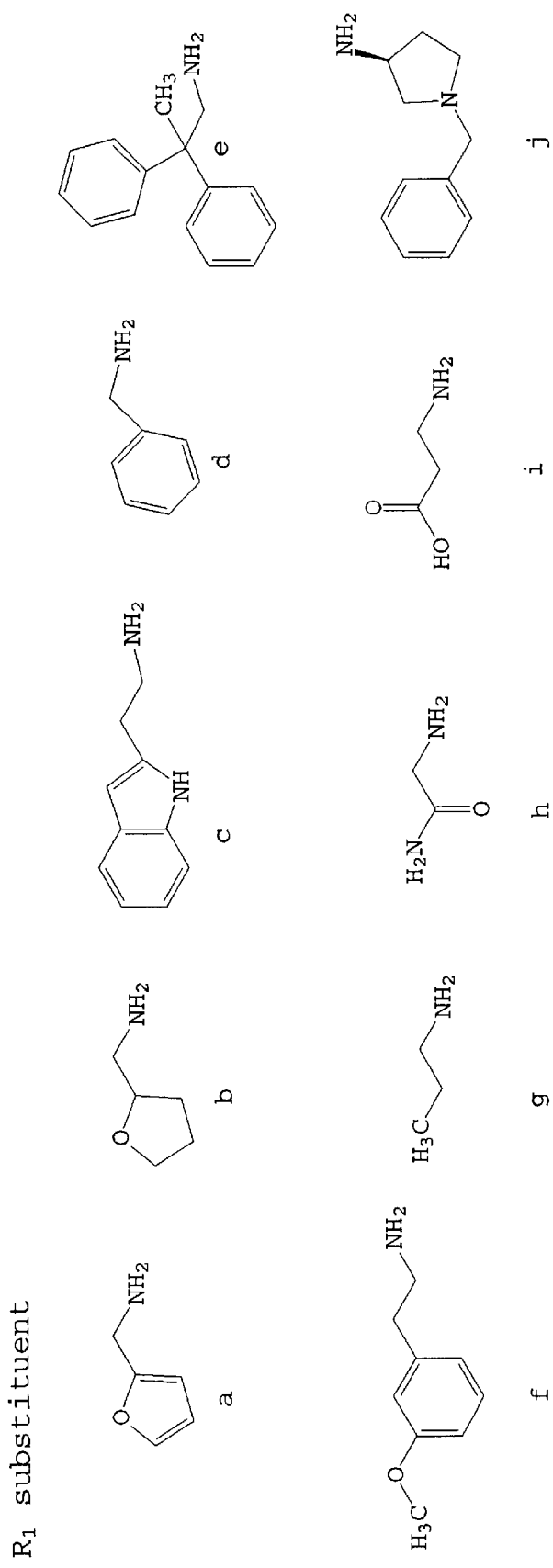
FIGS. 5A–5C illustrates the components used to prepare the Diverse Library. Diverse library components are labeled by lower case letter code as for the directed library.
Figure 5B:
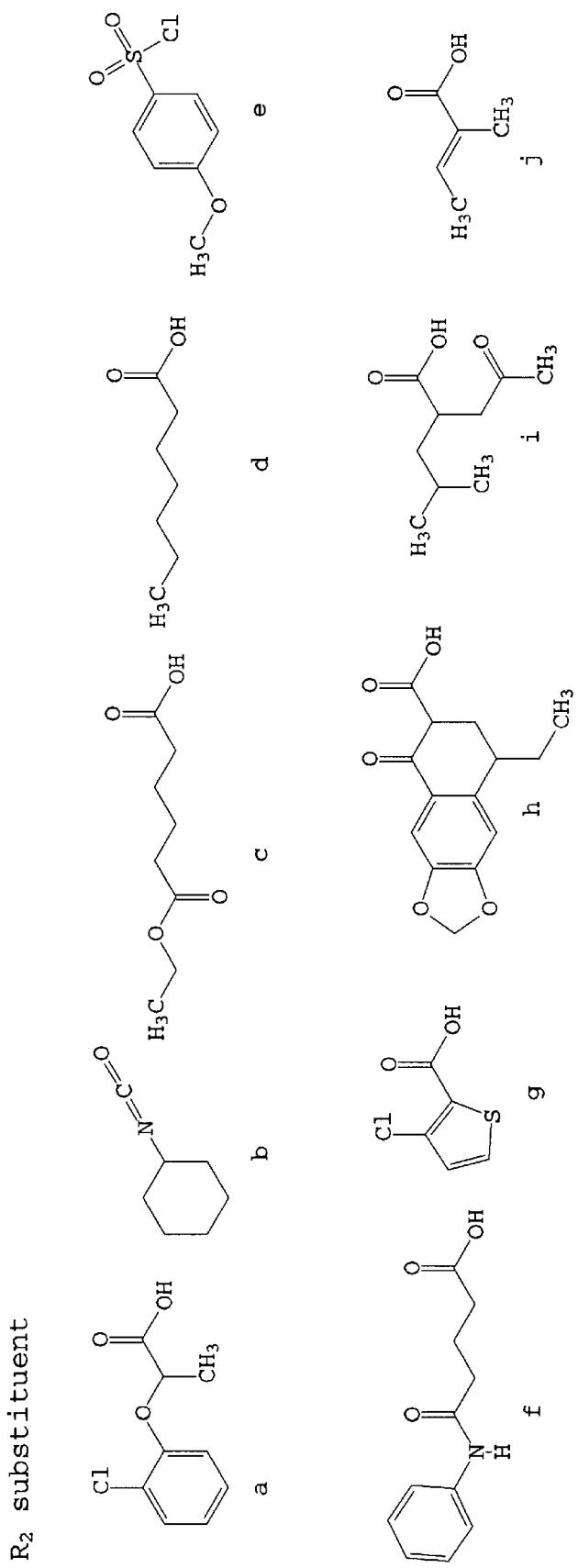
Figure 5C:
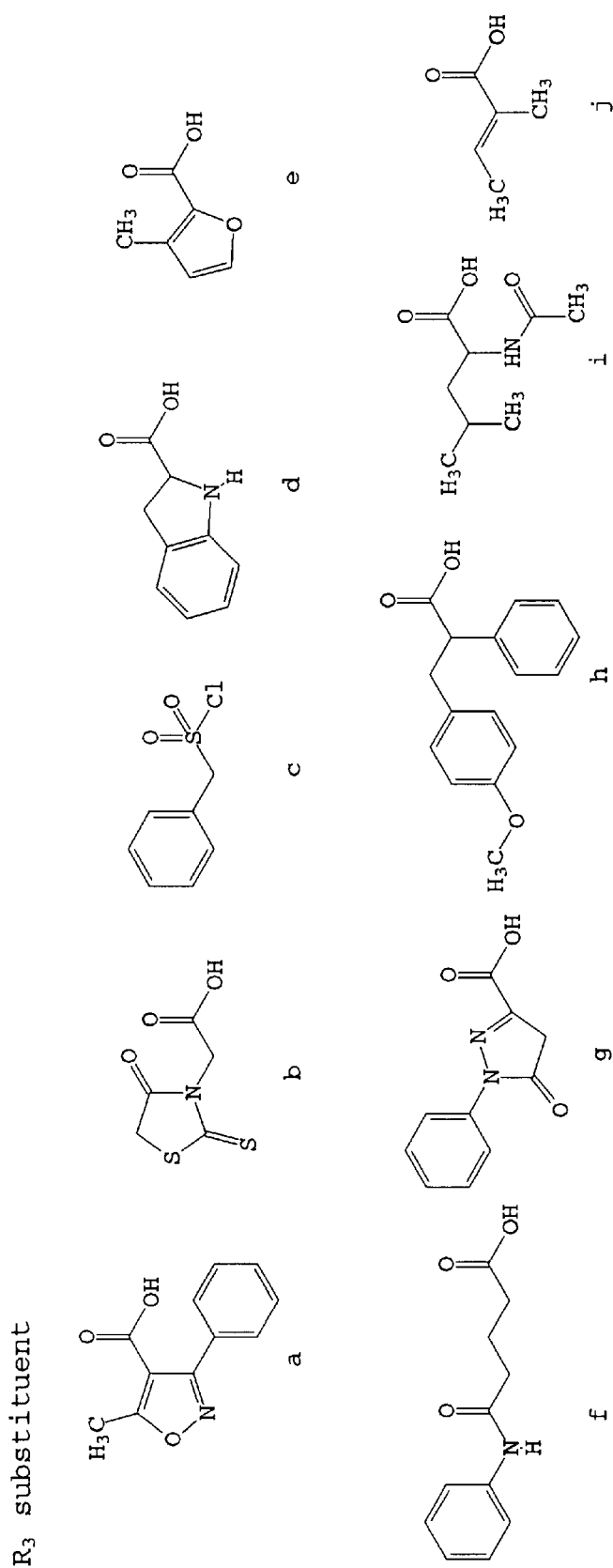
Figure 6A:
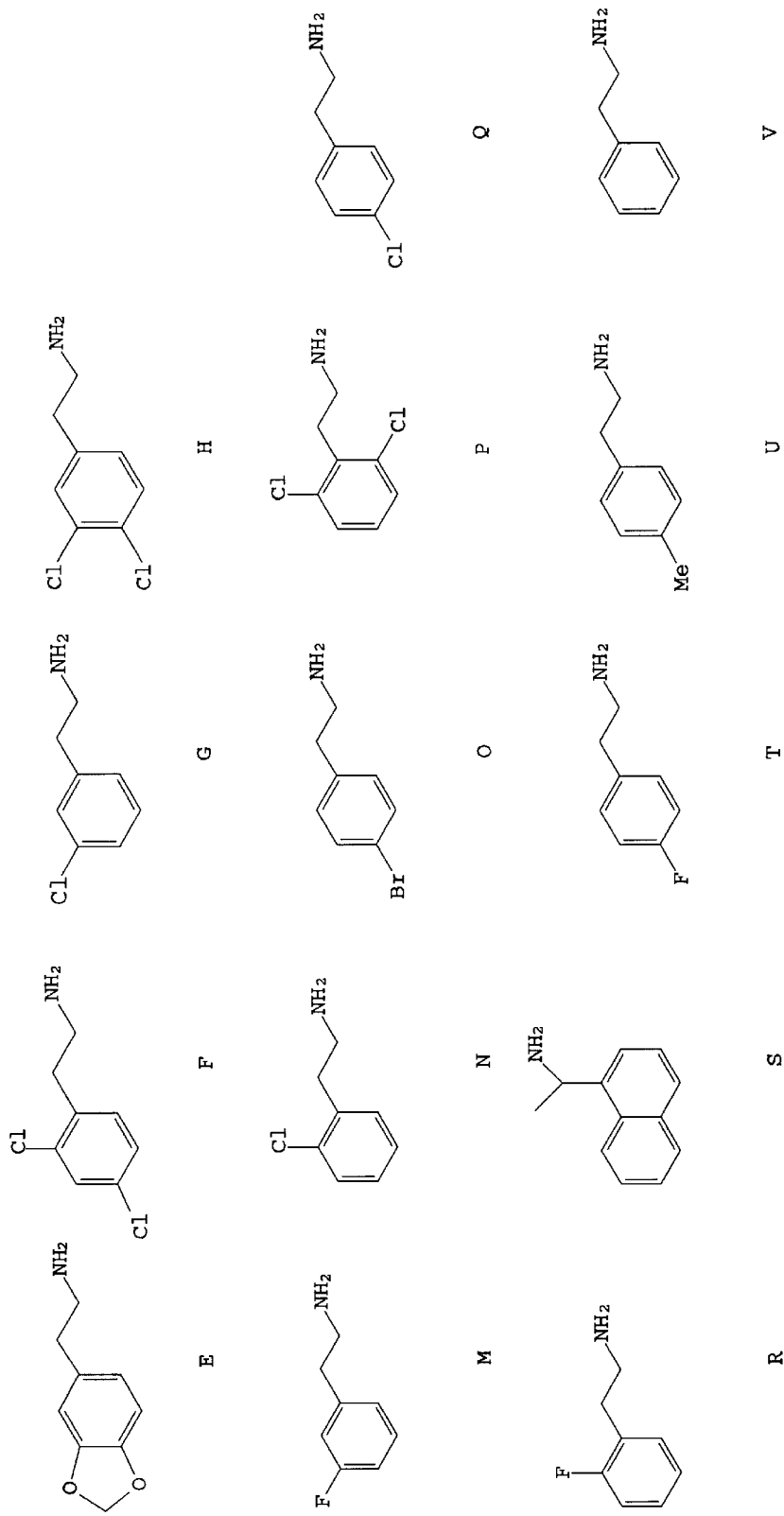
FIGS. 6A–6C illustrates the components in each of the clusters (see Experimental Design) that contained the most active sidechains, $R_1$=E, F; $R^2$=F, H; $R^3$=A, D. J. Thirty-nine compounds incorporating these sidechains were synthesized on resin as described previously, EFD, EHD, FFD, FHD, KFD, KHD, LFD, LHD, MFD, MHD, NFD, NHD, OFD, OHD, PFD, PHD, QFD, QHD, RFD, RHD, SFD, SHD, TFD, THD, UFD, UHD, VFD, VHD, EHA, EHJ, EHK, EHL, EHM, EHN, EHO, EHP, EHQ, EHR, EHS. The compounds were assayed at 333 nM, 100 nM and 33 nM in high-throughput screening. The most active compounds were synthesized on large scale and the $K_i$ values were determined (Table 3).
Figure 6B:
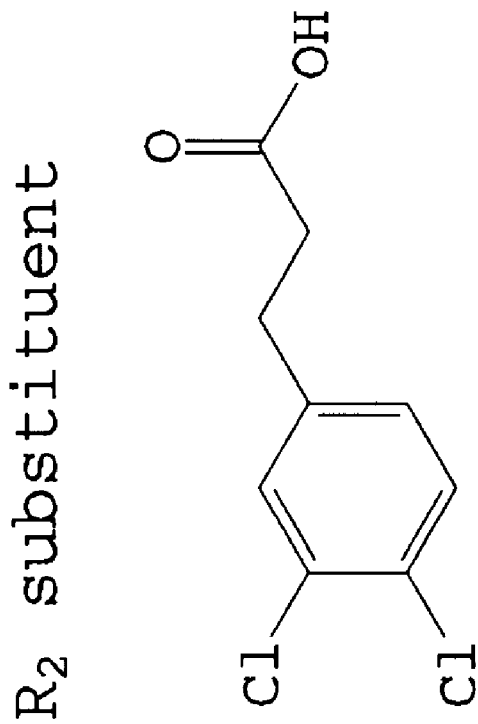
Figure 6B:
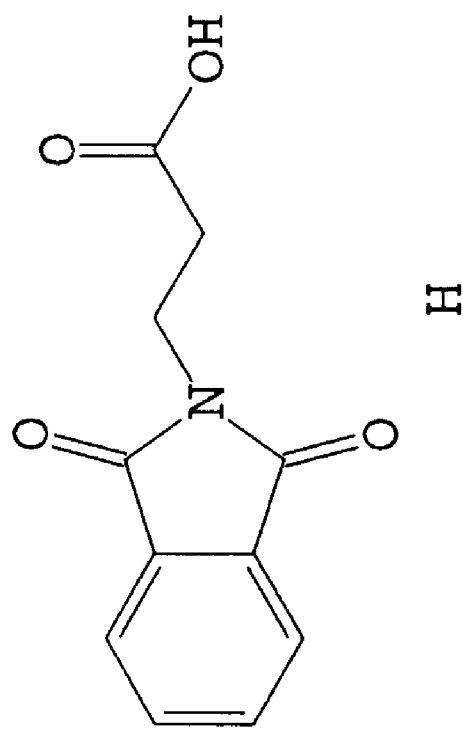
Figure 6C:
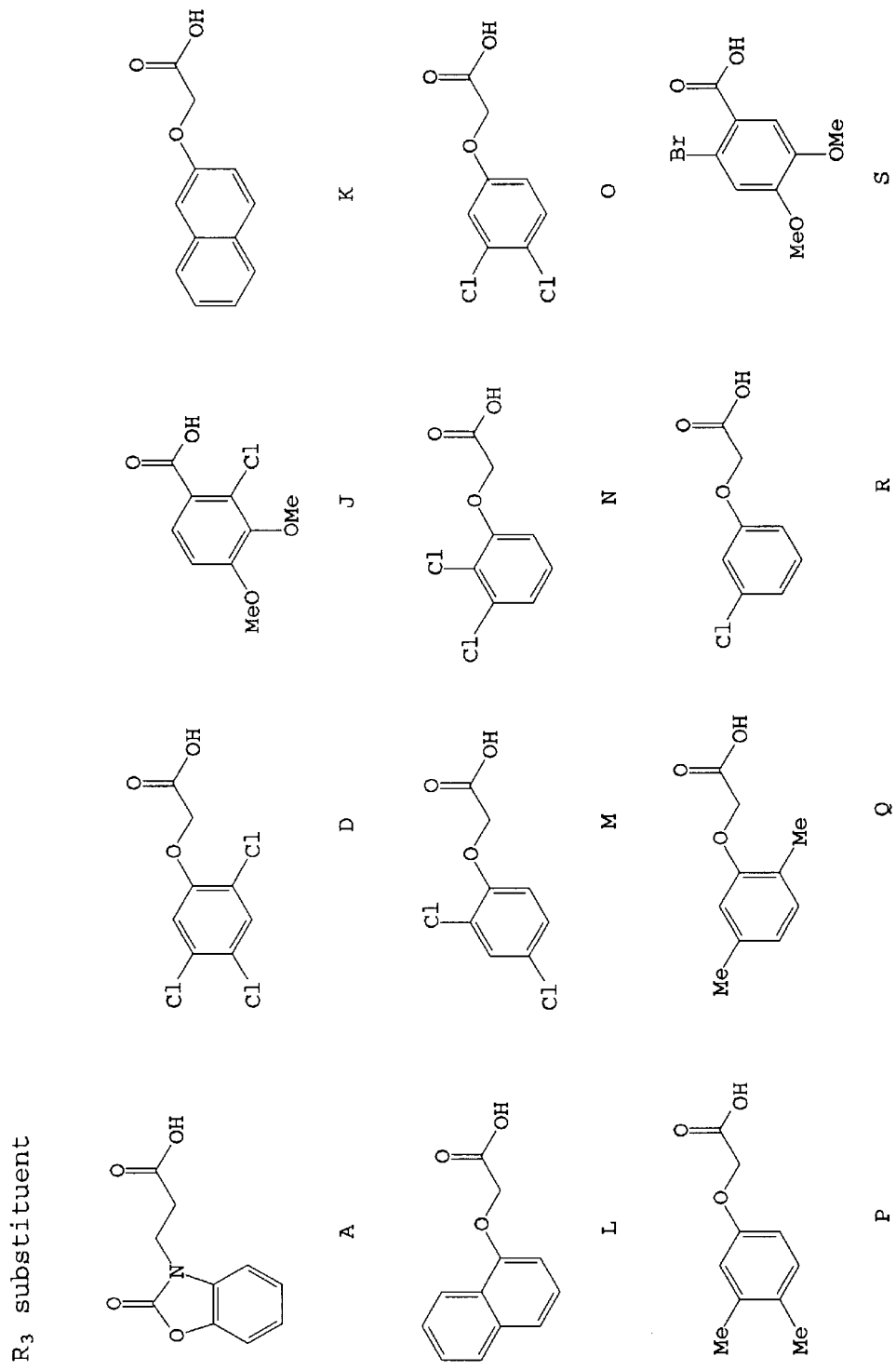

The directed and diverse libraries (1000 compounds each) were prepared using diastereomer 1 of the hydroxyethylamine scaffold with the components used in library syntheses shown in FIGS. 4 and 5, respectively. Because the pilot study with R and S epimers only showed activity at 1 $\mu$M inhibitor concentration for the S epimers, only the S epimers of the directed and diverse library were synthesized. All libraries were synthesized in a spatially separate format, and were screened in a high-throughput fluorometric assay for inhibitory activity against cathepsin D (G. A. Krafft, et al., *Methods Enzymol.* 241, 70–86 (1994))

1. Library Synthesis

The optimization of the solid-phase synthesis sequence to prepare the hydroxyethylamine inhibitors and the demonstration of reaction generality was previously reported by E. K. Kick and J. A. Ellman (*J. Med. Chem.* 38, 1427–1430 (1995)). Further testing was performed to establish that the different functionality to be displayed at $R_1$, $R_2$ and $R_3$ would be successfully incorporated into the potential inhibitors. First, all the amines and acylating agents to be incorporated in both the diverse and directed libraries were treated with trifluoroacetic acid for 2 h at room temperature to ensure stability to the support-cleavage conditions, by far the harshest reaction conditions in the synthesis sequence. Second, components that might pose difficulties on chemical or steric grounds were evaluated by trial syntheses. Five amines and four carboxylic acids that did not provide the expected final compound in high yields or purity were discarded. The following amines and acylating agents were successfully tested in the synthesis sequence: $R_1$=B, C, E, F, a, e, h, i, j; $R_2$=B, C, D, E, H, a, e, f; $R_3$=A, D E H, a, b, e, g, h, i (FIGS. 4 and 5). The remaining components were assumed to be compatible with the synthesis sequence.

The library synthesis was performed on polystyrene beads (20–40 mesh). The library was synthesized in a spatially separate array using a 96-ell filter apparatus. Transfer of the resin to the individual wells was performed using an isopycnic mixture of N,N-dimethylformamide (DMF) and 1,2-dichloroethane. Incorporation of $R_1$ was carried out using 1.0M free amine in N-methylpyrrolidinone (NMP) at 80° C. for 36 h. Incorporation of $R_2$ was carried out using stock solutions of 0.3 M carboxylic acid, 0.3M benzotriazole-1-yl-oxy-tris-pyrrolidino-phosphonium hexafluorophosphate (PyBOP), 0.3M 7-aza-1-hydroxybenzotriazole (HOAt), and 0.9M iPr2EtN in NMP overnight. The coupling reactions were performed twice to ensure that complete coupling had occurred. After azide reduction with $SnCl_2$, PhSH and $Et_3N$, incorporation of $R_3$ was carried out as reported above for $R_2$. Carboxylic acid $R_2$ =E was coupled using 0-(7-azabenzotriazol-1-yl)-1,1,3,3-tetramethyl-uronium hexafluorophosphate (HATU) instead PyBOP due to formation of a precipitate under the standard coupling procedure. The isocyanate $R_2$=b was coupled at 0.3M in NMP overnight, and the sulfonyl chlorides $R_2$=e and $R_3$=c were coupled at 0.3M in NMP that was 0.9M in $iPr_2EtN$. Cleavage of the material from the support was achieved by subjecting the resin to 95:5 trifluoroacetic acid: $H_2O$ for 30 mm. The cleavage mixture was removed from the resin via filtration, followed by rinsing the resin and concentration of the filtrates using a Jouan 10.10 centrifugation concentrator. Toluene was added to form an azeotrope with trifluoroacetic acid during the concentration step. After concentration, the libraries were stored at −20° C.

Compounds from each library, picked by random number generation, were analyzed by mass spectrometry in a matrix of α-cyano cinnamic acid on a Perseptive Biosystems MALDI instrument. For the diverse library the expected molecular ion peaks were observed for 46 of 49 compounds (poor ionization was obtained for the other three). Molecular ion peaks were obtained for 44 of 49 compounds from the directed library. In addition, the synthesis has been validated by the reasonable correlation of the approximate $IC_{50}$ values of the crude material from the libraries with purified material that was synthesized on large scale for a number of compounds (see, Table 3, infra).

2. Screening of the Libraries for Compounds Having Inhibitory Activity Against Cathepsin D Briefly, a fluorometric high through-put assay for activity toward human liver cathepsin D (Calbiochem) was performed in 96-well microtiter plates (G. A. Krafft, et al., *Methods Enzymol.* 241, 70–86 (1994)). The peptide substrate (Ac-Glu-Glu(Edans)-Lys-Pro-Ile-Cys-Phe-Phe-Arg-Leu-Gly-Lys(Methyl Red)-Glu-$NH_2$) used in the assay has been previously reported ($K_m$=6 $\mu$M) (E. T. Baldwin, et al., *Proc. Natl. Acad. Sci., U.S.A.* 90, 6796–6800 (1993)). The assay was performed in DYNATECH Microfluor fluorescence microtiter plates, and readings were taken on a Perkin-Elmer LS-50B with an attached 96-well plate reader. The excitation wavelength was 340 nm. A 340 nm interference filter (Hoya, U-340) for excitation and a 430 nm cut-off filter for emission were used. For the microtiter-based assays, the substrate concentration was 5 $\mu$M and the cathepsin D concentration was 9 nM in a 0.1M formic acid buffer (pH=3.7). DMSO (10%) was used to ensure complete dissolution of the inhibitors. The fluorescent unit readings were taken at three time points within the linear region of the substrate cleavage, and percent activity of the enzyme was determined by comparing the change of fluorescent units (FU) for each well to the average change in FU for six control wells without inhibitor. Each library was screened at approximately 1 $\mu$M inhibitor with the concentration based on the assumption that 50% of the theoretical yield was obtained for each inhibitor. All wells that showed <50% cathepsin D activity were screened at subsequent three-fold dilutions. All active compounds that showed <60% enzyme activity in 1 $\mu$M or lower inhibitor concentrations were assayed in duplicate).

E. Assay Results

At approximately 1 $\mu$M of crude compound, the directed library yielded 67 compounds that inhibited cathepsin D activity $\geq$50% (G. A. Krafft, et al., *Methods Enzymol.* 241, 70–86 (1994)). Further dilution of 333 nM and 100 nM inhibitor concentrations afforded 23 and 7 compounds, respectively, that inhibited cathepsin D activity $\geq$50% (see, Table 2). The data for the diverse library are also in Table 2, infra. There are many uncertainties that can influence the results of a high-throughput fluorescence assay, including the purity of each compound, the concentration of the compounds, and the experimental errors associated with the microtiter fluorescence assay. From repetitive experiments, these errors were estimated to be approximately 30%, expressed as enzyme activity.

TABLE 2

Number of Compounds with $\geq$ 50% Inhibition of Cathepsin D in Library Screen[a]

| [Inhibitor] | Library Directed | Diverse # |
|---|---|---|
| 100 nM | 7* | 1§ |
| 330 nM | 23† | 3¶ |
| 1 $\mu$M | 67 | 26 |
| 10 $\mu$M | 11/95tt | |

[a]Inhibitors of cathepsin D at respective concentrations:
*EAA, EFA, EHA, EHD, EHI, EHJ, FHA. An additional six compounds provided 40–50% inhibition of cathepsin D.
†EAA, EFA, EHA, FAA, FFA, FHA, EHB, EFD, EHD, EEF, EHF, FHF, EFH, EHH, FAH, FFH, EFI, EHI, EAJ, EFJ, EGJ, EHJ, FHJ. An additional thirty compounds provided 40–50% inhibition of cathepsin D.
‡One hundred compounds were selected by random number generation for testing at 10 $\mu$M. Five compounds were highly fluorescent at these concentrations, so that accurate assay data could not be obtained in these cases.
§fbb, ¶fba, fbb, fcb. Four compounds (fca, fdb, fib, hhb) provided 40–50% inhibition of cathepsin D; with the experimental error in the assay, this activity is similar to the activity for the three that are listed.
The diverse library was not tested at 10 $\mu$M.

In order to obtain accurate inhibition constants ($K_i$) several of the compounds most likely to be potent inhibitors based on the library screening were synthesized on a larger scale, purified by chromatography, and characterized by NMR and mass spectrometry. The $K_i$ values were calculated from $IC_{50}$ determinations (see, Table 3). From the compounds that were fully characterized, one compound was obtained from the directed library with a $K_i$ below 100 nM, whereas the diverse library contained inhibitors that were 3–4 times less potent.

TABLE 3

Inhibition Constants for a Number of the Compounds That Are Potent Inhibitors[a]

| Cpd Code | Scaffold | $K_i$ (nM) |
|---|---|---|
| EHD | 1 | 73 ± 9 |
| EHD | 2 | >5000 |
| EHJ | 1 | 111 ± 8 |
| EHA | 1 | 131 ± 12 |
| EFA | 1 | 171 ± 25 |
| FHA | 1 | 231 ± 31 |
| fbb | 1 | 356 ± 31 |
| fdb | 1 | 595 ± 66 |

[a]The cathepsin D assay for "hits" from the directed and diverse libraries was performed in a quartz cuvette with a Perkin-Elmer LS-50B spectrometer. The substrate concentration was 2.5 $\mu$M and the cathepsin D concentration was 10 nM. Inhibition constants ($K_i$) were determined from $IC_{50}$ values taken from plots of $V_i V_0$ versus inhibitor concentration, where $V_0$ is the velocity in absence of the inhibitor and $V_i$ is the velocity with inhibitor. Since the substrate concentration is significantly below $k_m$, the $IC_{50}$ values were converted to $K_i$ by the equation $K_i \approx (IC_{50} - E_t/2)$, where $E_t$ = enzyme concentration (S. Cha, et al., Biochem. Pharmacol., 24, 2187–2197 (1975)).

F.(i) Second Generation Library

In the design of the directed library, derivatives with a high level of structural similarity were selected against by applying a clustering algorithm to the highest scoring components (see Directed Library Design). These clusters were re-examined to explore the important structural elements of the most active compounds from the directed library. In particular, a small second generation library from the clusters for the $R_1$, $R_2$ and $R_3$ positions that provided the most active compounds was synthesized and screened (see, FIG. 6). At 1 $\mu$M, 92% of the compounds screened inhibited cathepsin D $\leq$50%, and 18% of the compounds at 100 nM inhibited cathepsin D$\leq$50%.

Inhibition constants were determined for selected compounds (see, Table 4), providing several potent inhibitors ($K_1 \leq$15 nM) of cathepsin D.

TABLE 4

Second Generation Assay (see, FIG. 6)[a]

| Cpd. Code | Scaffold | $IC_{50}$ (nM) | $K_i$ (nM) |
|---|---|---|---|
| EHO | 1 | 19 ± 2 | 15 |
| EHO | 2 | >5000 | |
| FHO | 1 | 18 ± 2 | 14 |
| EHM | 1 | 14 ± 2 | 9 |
| EHR | 1 | 20 ± 2 | 15 |
| EHS | 1 | 64 ± 6 | 59 |
| UHD | 1 | 229 ± 44 | 224 |

[a]Assay conditions are reported in Table 3.

F.(ii) Additional Compounds

Known aspartyl protease inhibitors have both (R) and (S) stereocenters about the hydroxyl group in Formula I. Employing a-alkoxy chelation and non-chelation controlled reductions, the following synthetic strategy demonstrates acyclic diastereocontrol on solid support providing access to either desired diastereomer. By exploring different functional groups for $R_5$ and $R_6$ and selecting the $R_1$, $R_2$, and $R_3$ substituents providing the most potent Cathepsin D inhibitors, additional low nanomolar Cathepsin D inhibitors were discovered.

Figure 7:
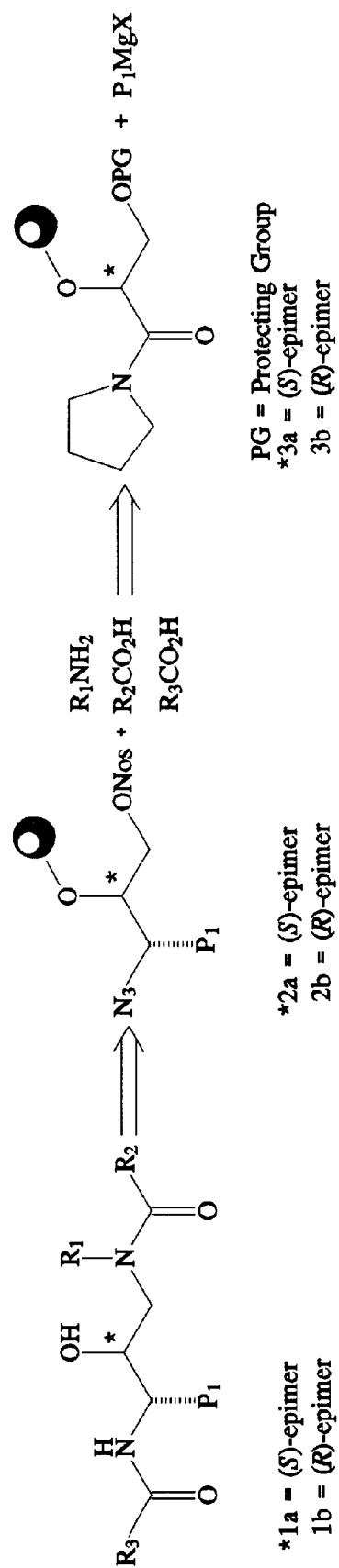
FIG. 7 illustrates structural diversity being introduced via Grignard addition to solid support-bound - alkoxy pyrrolidine amide.

Structural diversity may be derived through Grignard addition to a solid support-bound α-alkoxy pyrrolidine amide 3 (see FIG. 7). The source of diversity is derived from aromatic and alkyl Grignard reagents. The Grignard reagents that are not commercially available can be synthesized using activated magnesium turnings, or a magnesium anthracene THF complex and the corresponding aromatic and alkyl halides. Grignard reagents are a suitable source to introduce diversity in the $P_1$ site of potential aspartyl protease inhibitors, since the $S_1$ protease surface tends to be hydrophobic. The resulting ketone is reduced using chelation and non-chelation conditions to provide the desired diastereomer. After several functional group manipulations, known azido-nosylate intermediate 2 is derived and carried through the previously reported synthesis to obtain potential aspartyl protease inhibitor 1 (see E. K. Kick, J. A. Ellman, J. Med. Chem. 38, 1427–1430 (1995)) (see, FIG. 7).

The pyrrolidine amide 4 prepared in 3 steps in an overall 76% yield from commercially available methyl (s)-(−)-2,2-dimethyl-1,3-dioxolane-4-carboxylate, was coupled to benzyloxybenzyl bromide resin 5 using sodium hydride, tetrabutylammonium iodide, and catalytic 18-Crown-6 in THF for 2 hours at 45° C. (see FIG. 8). Bromide resin 5 was derived from carbon tetrabromide, triphenylphosphine, and commercially available Wang resin.

Figure 8:
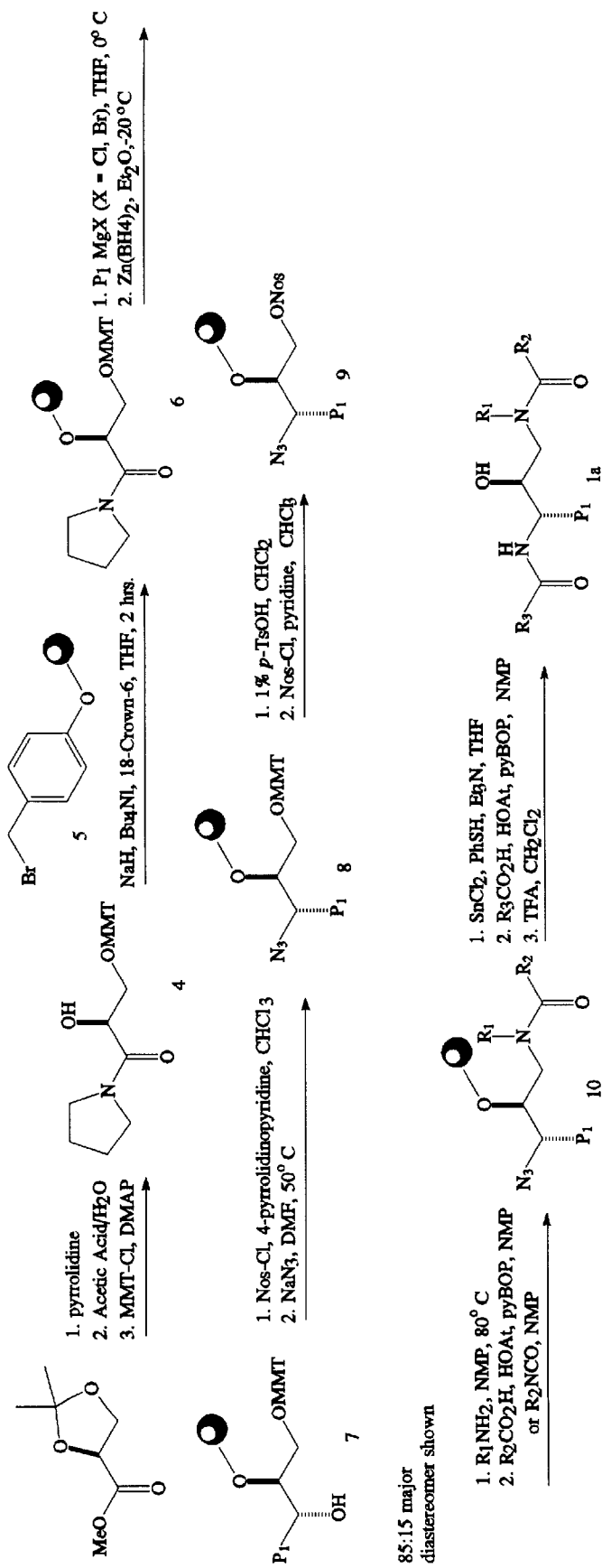
FIG. 8 illustrates synthesis of solid phase aspartyl protease inhibitor synthesis.
Figure 9A:
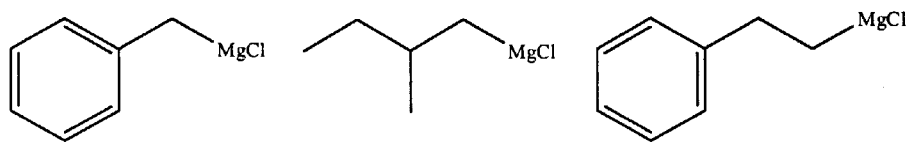
FIGS. 9A–9B illustrate components to generate library diversity in a 204 compound library.
Figure 9A:
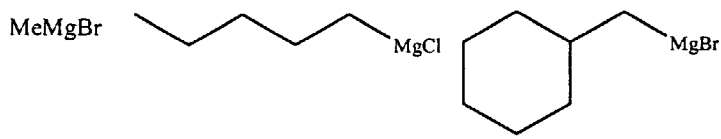
Figure 9A:
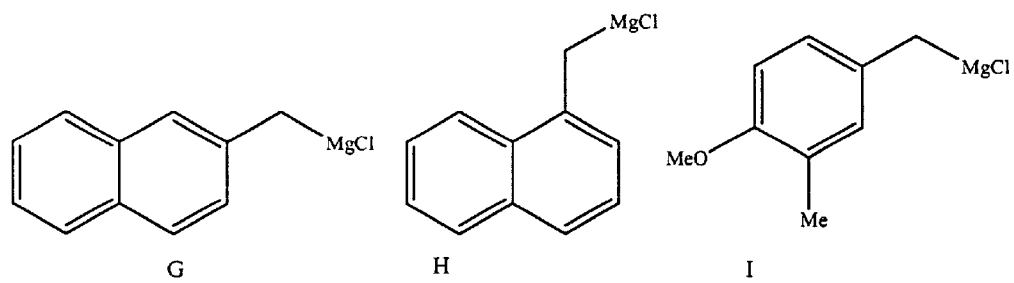
Figure 9A:
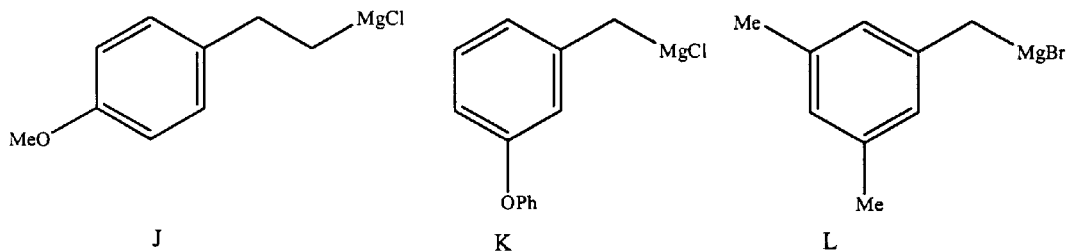
Figure 9A:
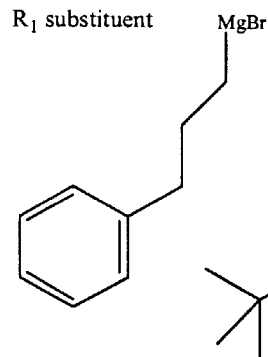
Figure 9B:
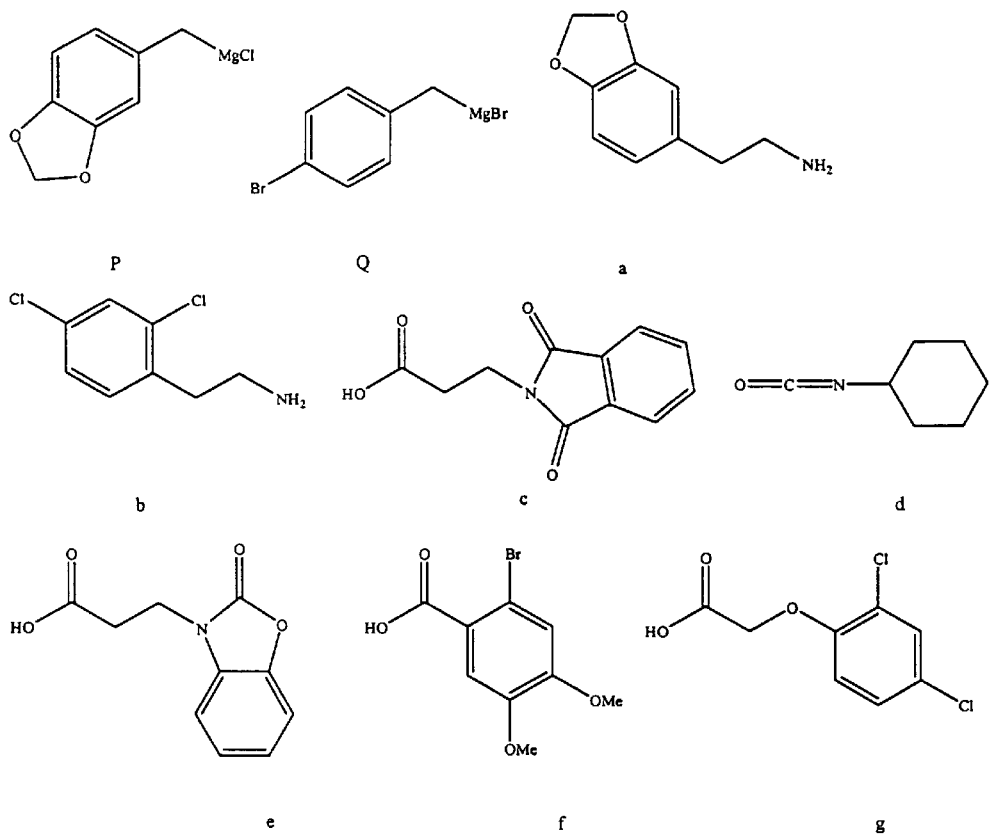

Grignard addition in THF at 0° C. to support-bound pyrrolidine amide 6 followed by -alkoxy chelation controlled reduction of the resulting ketone using zinc borohydride in diethyl ether at −20° C. afforded secondary alcohol 7 in a 85:15 diastereomeric mixture with the major diastereomer shown (see FIG. 8). A small portion of secondary alcohol 7 was cleaved from the support to provide the corresponding triol product which was converted to the corresponding triacetate using acetic anhydride and DMAP (Dimethyl amino pyridine). Diastereoselectivity was determined from GC analysis of the corresponding triacetates. No over alkylation from the Grignard addition was detected for all components used in the library.

Secondary alcohol 7 was converted to azide 8 through the formation of a secondary nosylate using 4-nitrobenzenesulfonyl chloride and 4-pyrrolidinopyridine in chloroform followed by azide displacement with sodium azide in N,N-dimethylformamide at 50° C. The p-methoxy trityl protecting group was selectively removed using 1% p-toluenesulfonic acid in methylene chloride. Nosylation of the primary alcohol with 4-nitrobenzenesulfonyl chloride and pyridine in chloroform provided azido-nosylate 9.

Amine displacement in N-methylpyrrolidinone (NMP) at 80° C. followed by acylation with the desired carboxylic acid, benzotriazole-1-yl-oxy-tris-pyrrolidino-phosphonium hexafluorophosphate (PyBOP), aza-l-hydroxybenzotriazole (HOAt) or isocyanate in NMP afforded intermediate 10 with the $P_1$, $R_1$, and $R_2$ sites of diversity in place. Reduction of the azide with tin(II) chloride, thiophenol, and triethylamine followed by acylation with the $R_3$ carboxylic acid, PyBOP, and HOAt, and lastly, cleavage from the support using a trifluoroacetic acid:methylene chloride (90:10) mixture provided the desired potential aspartyl protease inhibitor 1a.

A library of 204 compounds was derived from the components in FIG. 9. The most potent inhibitors of Cathepsin D were synthesized on a larger scale, purified, and biologically assayed to determine $K_i$ values as detailed in Table 5. Overall yields of these scaled-up inhibitors ranged from 46–48% for the entire 12 step solid-phase synthesis as determined by the mass balance of desired product after column chromatography purification.

TABLE 5

Inhibition constants for selected compounds ($K_i$)

| Inhibitor | Code ($P_1 R_1 R_2 R_3$) | $K_i$ (nM) | Overall Yield (12 steps) |
|---|---|---|---|
| 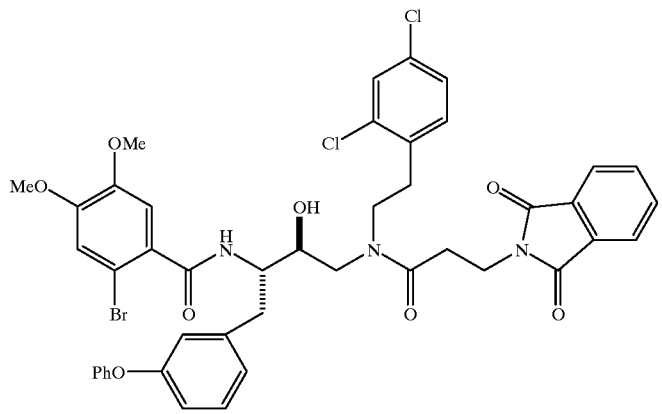 | Kbcf | 1.9 ± 0.2 | 46% |

TABLE 5-continued

Inhibition constants for selected compounds ($K_i$)

| Inhibitor | Code ($P_1$ $R_1$ $R_2$ $R_3$) | $K_i$ (nM) | Overall Yield (12 steps) |
|---|---|---|---|
| 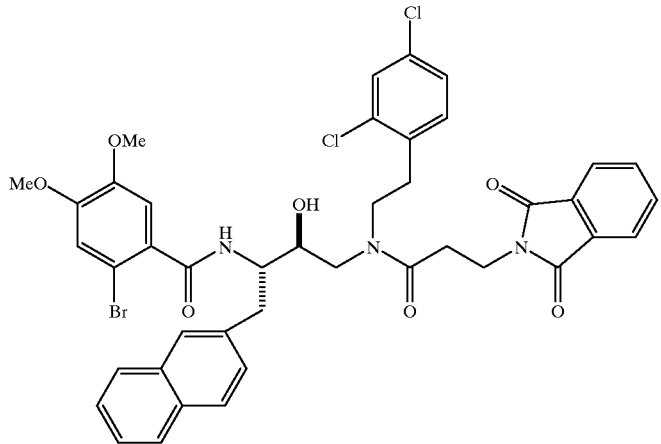 | Gbcf | 2.6 ± 0.2 | 48% |
| 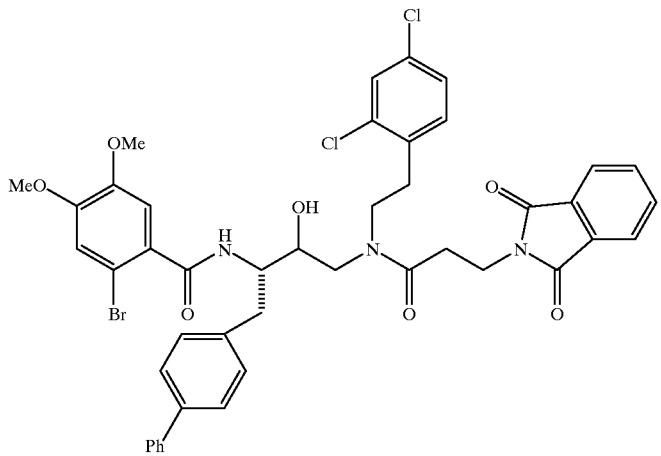 | Obcf | 2.6 ± 0.2 | 48% |
| 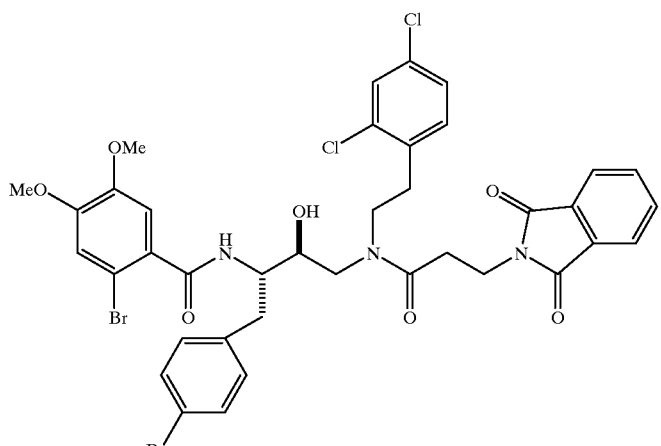 | Qbcf | 6.7 ± 0.7 | 46% |

Synthesis of inhibitors

Several of the most potent compounds were synthesized on an average of 115 milligram scale on the solid support following the aforementioned method. These compounds were purified by column chromatography and characterized by $^1$H NMR and elemental analysis. Overall yields of the compounds were based on the entire 12 step solid-phase synthesis and determined by the mass balance of desired product after column chromatography purification. The characterization data are listed with the corresponding compound code. The $^1$H NMR data is reported for the major amide rotamer of the major diastereomer for each compound.

Kbcf. (57 mg, 46%) $^1$H NMR (400 MHz, CDCl$_3$) d 2.65 (m, 2H), 2.88 (apparent t, J=7.7, 2H), 3.01 (apparent t, J=6.9, 2H), 3.24 (m, 1H), 3.47 (m, 2H), 3.83–3.96 (m, 4H), 3.85 (s, 3H), 3.89 (s, 3H), 4.34 (apparent q, J=8.3, 1H), 4.66 (br. s, 1H), 6.71 (d, J=9.2, 1H), 6.84 (dd, J=1.7, 8.0, 1H), 6.93–7.00 (m, 5H), 7.05 (m, 1H), 7.05 (s, 1H), 7.07 (s, 1H), 7.16 (dd, J=2.1, 8.1, 1H), 7.23–7.30 (m, 3H), 7.34 (d, J=2.1, 1H), 7.71 (dd, J=3.1, 5.4, 2H), 7.83 (dd, J=3.1, 5.4, 2H). Anal. calc'd for C$_{44}$H$_{40}$N$_3$O$_8$Cl$_2$Br$_1$: C, 59.41; H, 4.53; N, 4.72. Found: C, 59.22; H, 4.76; N, 4.52.

Gbcf. (48 mg, 48%) $^1$H NMR (400 MHz, CDCl$_3$) d 2.62 (apparent t, J=7.5, 2H), 2.82 (apparent t, J=7.6, 2H), 3.18–3.25 (m, 3H), 3.40–3.47 (m, 2H), 3.57 (s, 3H), 3.85 (s, 3H), 3.91–3.96 (m, 4H), 4.47 (apparent q, J=8.4, 1H), 4.76 (br. s, 1H), 6.69 (s, 1H), 6.92 (d, J=8.2, 1H), 6.95 (s, 1H), 7.04 (dd, J=2.1, 8.2, 1H), 7.29 (d, J=2.1, 1H), 7.40–7.45 (m, 3H), 7.68 (dd, J=3.0, 5.5, 2H), 7.71–7.80 (m, 6H). Anal. calc'd for C$_{42}$H$_{38}$N$_3$O$_7$Cl$_2$Br,: C, 59.52; H, 4.52; N, 4.96. Found: C, 59.63; H, 4.67; N, 4.69.

Obcf. (55 mg, 48%) $^1$H NMR (400 MHz, CDCl$_3$) d 2.65 (m, 2H), 2.85 (apparent t, J=7.3, 2H), 3.08 (apparent t, J=6.7, 2H), 3.23 (m, 1H), 3.44 (m, 1H), 3.57 (m, 1H), 3.75 (s, 3H), 3.86 (s, 3H), 3.94 (m, 4H), 4.39 (apparent q, J=8.3, 1H), 4.73 (br. s, 1H), 6.78 (d, J=9.2, 1H), 6.93 (s, 1H), 6.97 (s, 1H), 7.02 (d, J=8.2, 1H), 7.10 (dd, J=2.1, 8.2, 1H), 7.30 (d, J=2.1, 1H), 7.36–7.42 (m, 5H), 7.51–7.54 (m, 4H), 7.68 (dd, J=3.0, 5.4, 2H), 7.81 (dd, J=3.0, 5.4, 2H). Anal. calc'd for C$_{44}$H$_{40}$N$_3$O$_7$Cl$_2$Br$_1$: C, 60.49; H, 4.62; N, 4.81. Found: C, 60.23; H, 4.86; N, 4.58.

Qbcf. (55 mg, 46%) $^1$H NMR (400 MHz, CDCl$_3$) d 2.64 (m, 2H), 2.86 (apparent t, J=7.1, 2H), 2.96 (m, 2H), 3.20 (m, 1H), 3.46 (m, 1H), 3.54 (m, 1H), 3.78 (m, 2H), 3.82 (s, 3H), 3.86 (s, 3H), 3.91 (m, 2H), 4.31 (apparent q, J=8.5, 1H), 4.73 (br. s, 1H), 6.73 (d, J=9.3, 1H), 6.85 (s, 1H), 6.96 (s, 1H), 7.03 (d, J=8.3, 1H), 7.14 (m, 2H), 7.16 (dd, J=2.2, 8.3, 1H), 7.32 (d, J=2.2, 1H), 7.37–7.41 (m, 2H), 7.70 (dd, J=3.0, 5.5, 2H), 7.80 (dd, J=3.0, 5.5, 2H). Anal. calc'd for C$_{38}$H$_{35}$N$_3$O$_7$Cl$_2$Br$_2$: C, 52.08; H, 4.03; N, 4.79. Found: C, 52.28; H, 4.09; N, 4.60.

G. Results

Novel low nanomolar inhibitors of cathepsin D were identified rapidly using combinatorial chemistry coupled with two different computational strategies. The diverse and directed libraries together yielded over 90 compounds active at 1 µM and 26 active in the submicromolar range. The "hit rate" for activity at 1 µM is 6–7% for the directed library and 2–3% for the diverse library. Even though both the directed and diverse libraries are based on the "active" epimer of the scaffold, the results from the directed library are clearly superior. At all concentrations <1 µM, there were more "hits" in the directed library than the diverse library. The most potent inhibitors from the directed library are 3–4 fold better than those in the diverse library. It is clear from the results that the number and quality of the active compounds can be increased by using relevant information about the target.

A strength of the structure-based procedure is that it leads directly to testable geometrical hypotheses. In this study there are three hypotheses: 1) S epimers are predicted to bind better than the R epimers; 2) there are two energetically reasonable scaffold conformations (family 1+2, family 3+4), which place R groups into different pockets; 3) all the inhibitors are assumed to bind in approximately the same orientation as pepstatin.

The first hypothesis was directly tested in pilot experiments where no inhibitors based upon the R epimer had activity at 1 µM. In addition, the R epimer of one of the most potent compounds had a K$_i$ no better than 5 µM while the K$_1$ of the S epimer was 15 nM (see, Table 4). This conclusion and the inhibitor orientations in the cathepsin D complex will be examined crystallographically.

Using the methodology described herein, active compounds can be identified and then the activity is optimized. The optimization criteria can include improved potency, selectivity, pharmacokinetic properties, or reduced toxicity. Each of these issues appears amenable to library design. For example, compounds with five-six fold improved potencies were rapidly identified by synthesizing and screening a small second generation library that explored variants of the most active compounds.

The success of the directed library in finding potent inhibitors demonstrates the power of coupling combinatorial libraries with structure-based design. Combinatorial libraries allow a larger area of molecular space to be explored with the functionality selected by the structure-based design, removing the need to identify in advance a single "best" target. Similarly, computational methods allow rapid examination of extremely large virtual regimes >10$^{10}$ compounds) and focus the chemical efforts into productive regimes.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A compound having the formula:

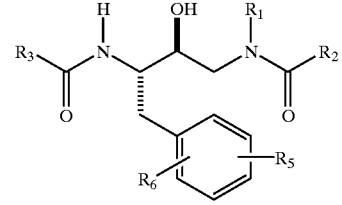

Formula I wherein:

R$_1$, R$_2$ and R$_3$ are members independently selected from the group consisting of alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl; provided R$_2$ is not a radical which is a nitrogen-bonded cyclic α-amino acid or ester thereof;

R$_5$ and R$_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or R$_5$ and R$_6$ and the carbons to which they are bound join to form an optionally substituted carbocyclic or heterocyclic fused ring system having a total of 9- or 10-ring atoms within said fused heterocyclic ring system, said heterocyclic fused ring system containing at least one member selected from the group consisting of a nitrogen atom, an oxygen atom and a sulfur atom.

2. The compound in accordance with claim 1 wherein $R_1$ is a member selected from the group consisting of heteroarylalkyl and substituted arylalkyl.

3. The compound in accordance with claim 1 wherein $R_1$ is a member selected from the group consisting of:

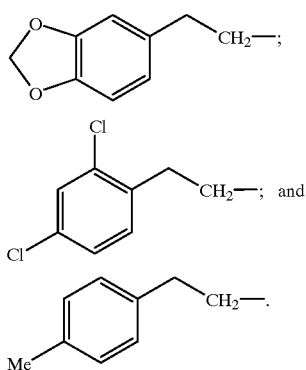

4. The compound in accordance with claim 1 wherein $R_2$ is a member selected from the group consisting of heteroarylalkyl, substituted arylalkyl and aryloxyalkyl.

5. The compound in accordance with claim 1 wherein $R_2$ is a member selected from the group consisting of:

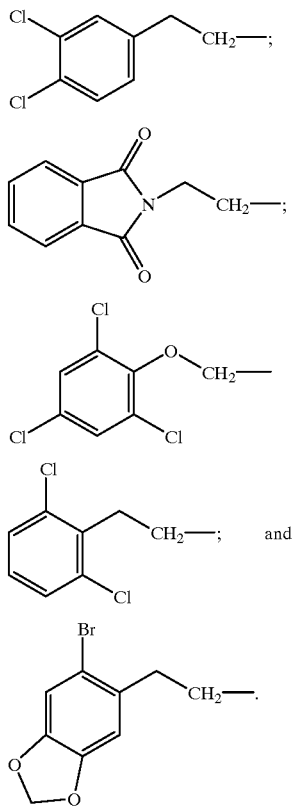

6. The compound in accordance with claim 1 wherein $R_3$ is a member selected from the group consisting of substituted aryl, heteroarylalkyl and aryloxyalkyl.

7. The compound in accordance with claim 1 wherein $R_5$, $R_6$ and the carbons to which they are bound join to form an optionally substituted napthalene ring.

8. The compound in accordance with claim 1 wherein $R_5$ and R6 are both hydrogen.

9. The compound in accordance with claim 1 wherein $R_5$ is hydrogen and $R_6$ is meta or para substituent selected from the group consisting of halogen, alkyl, substituted alkyl, aryl, substituted aryl, arylalkyl, substituted arylalkyl, aryloxyalkyl and substituted aryloxyalkyl.

10. The compound in accordance with claim 1 wherein $R_3$ is a member selected from the group consisting of:

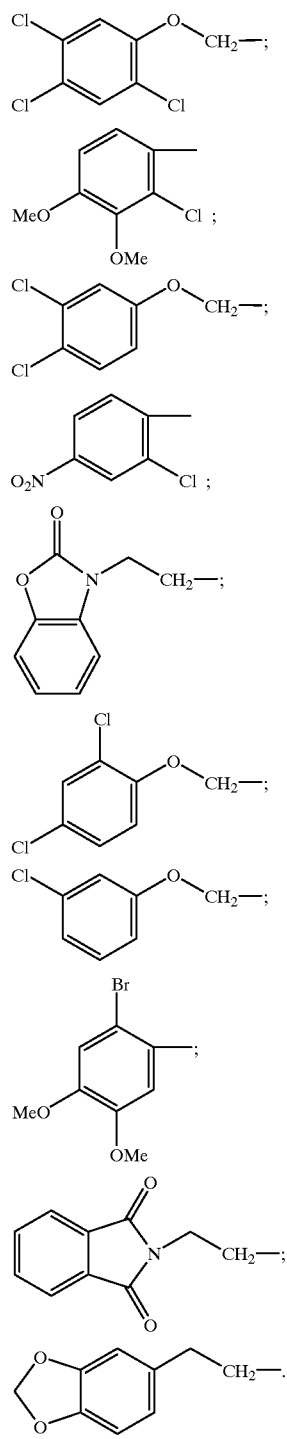

11. The compound in accordance with claim 1 wherein said compound is selected from the group consisting of

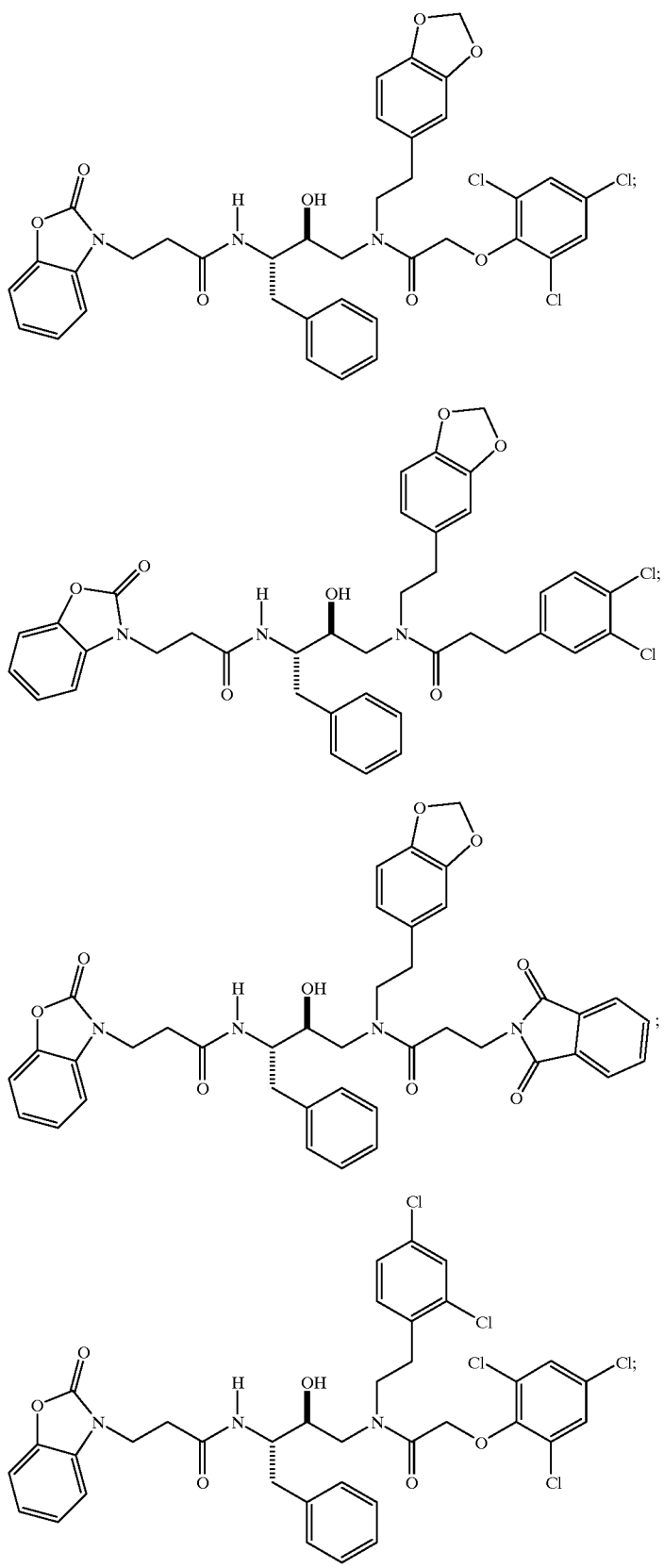

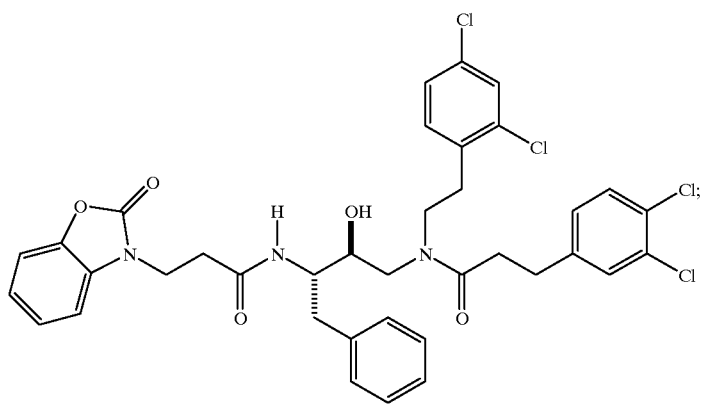
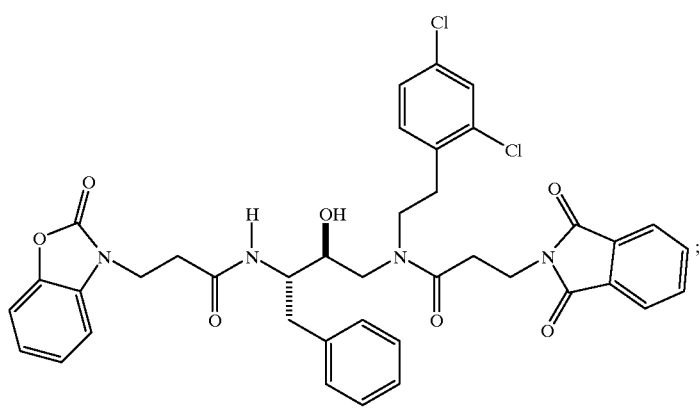
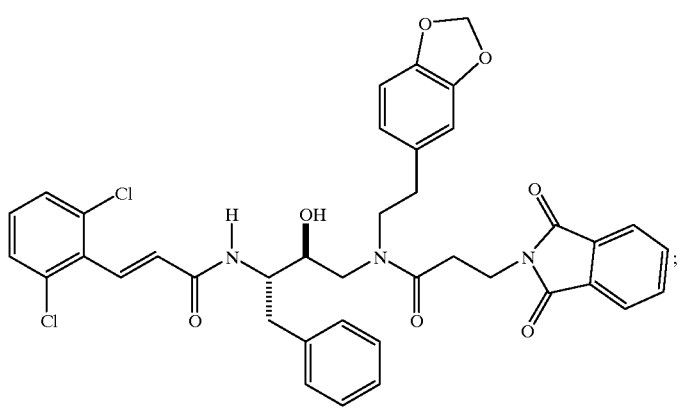
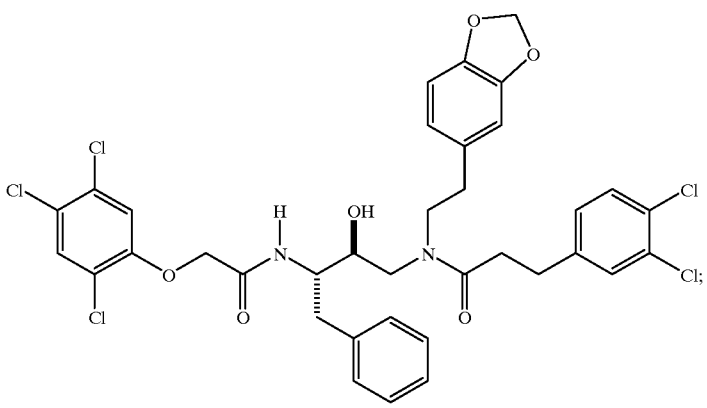

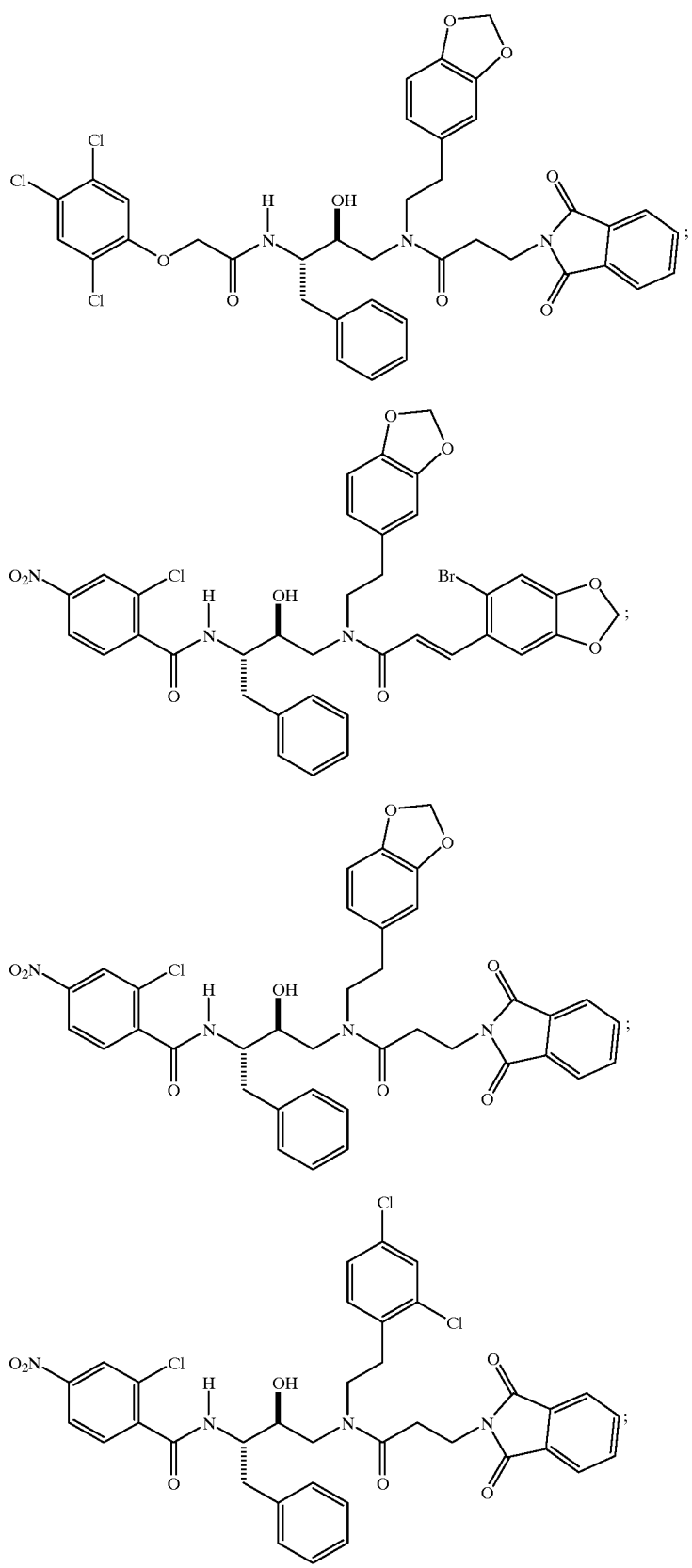

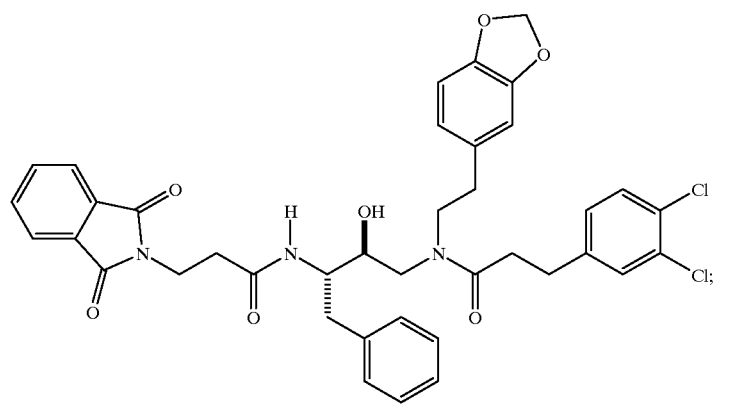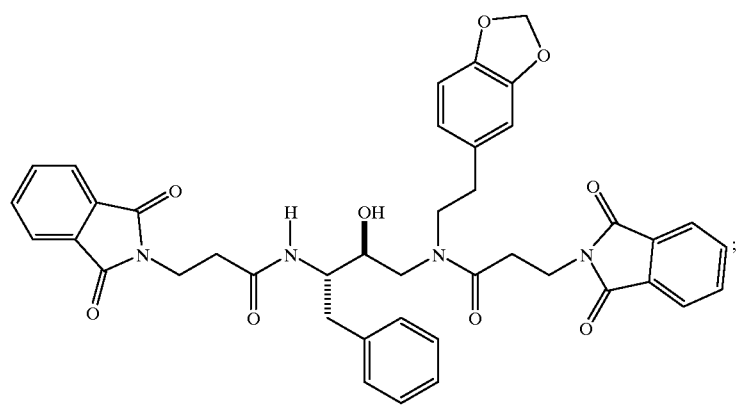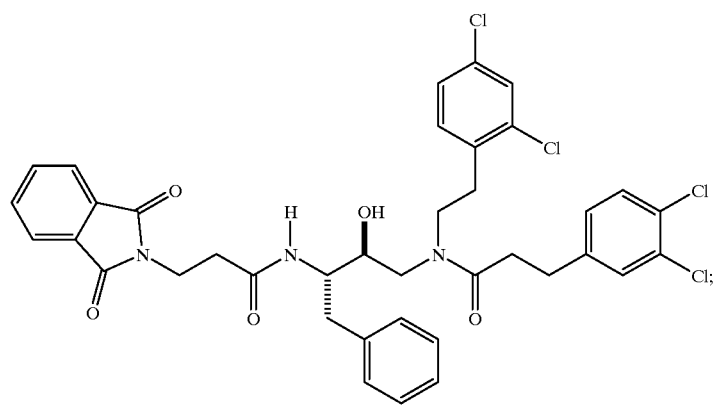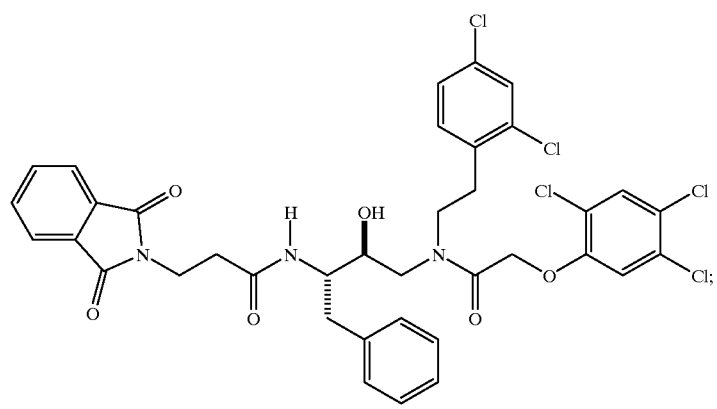

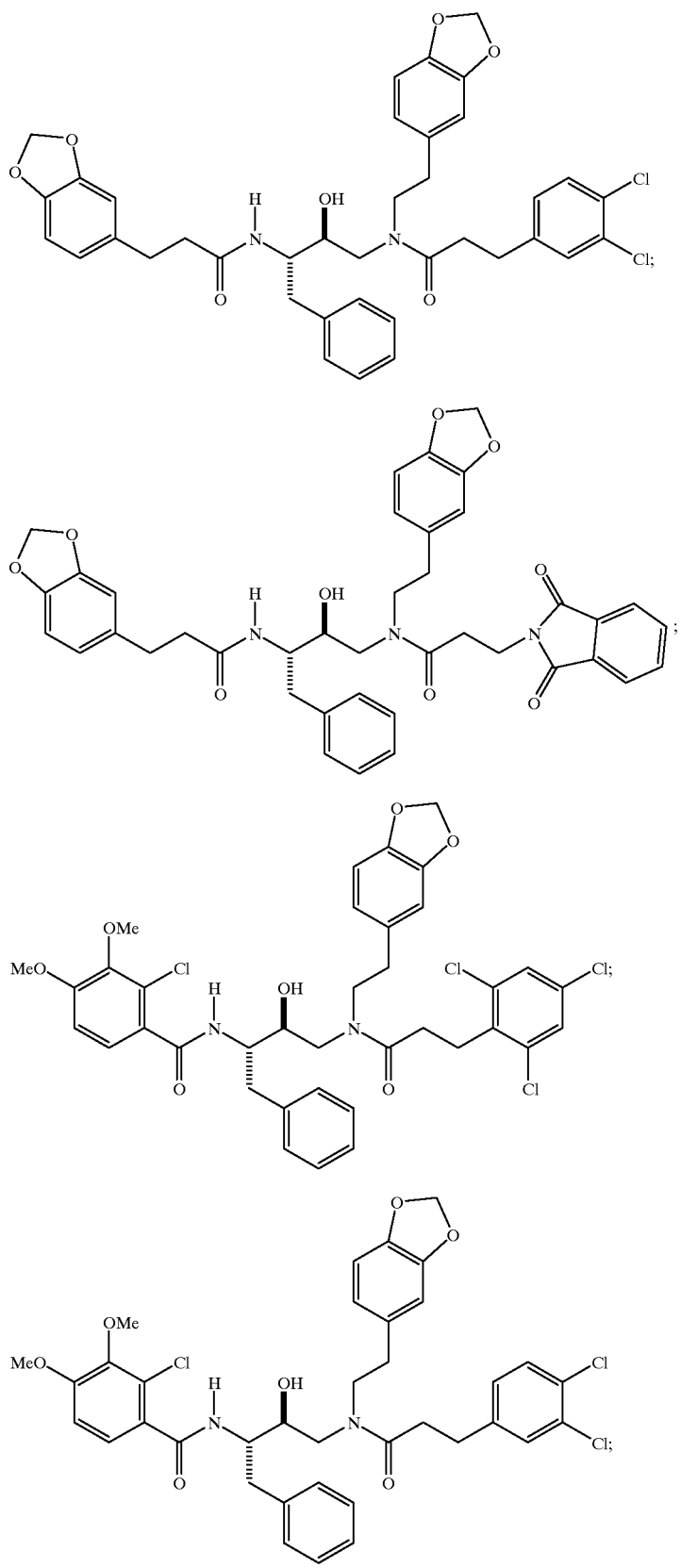

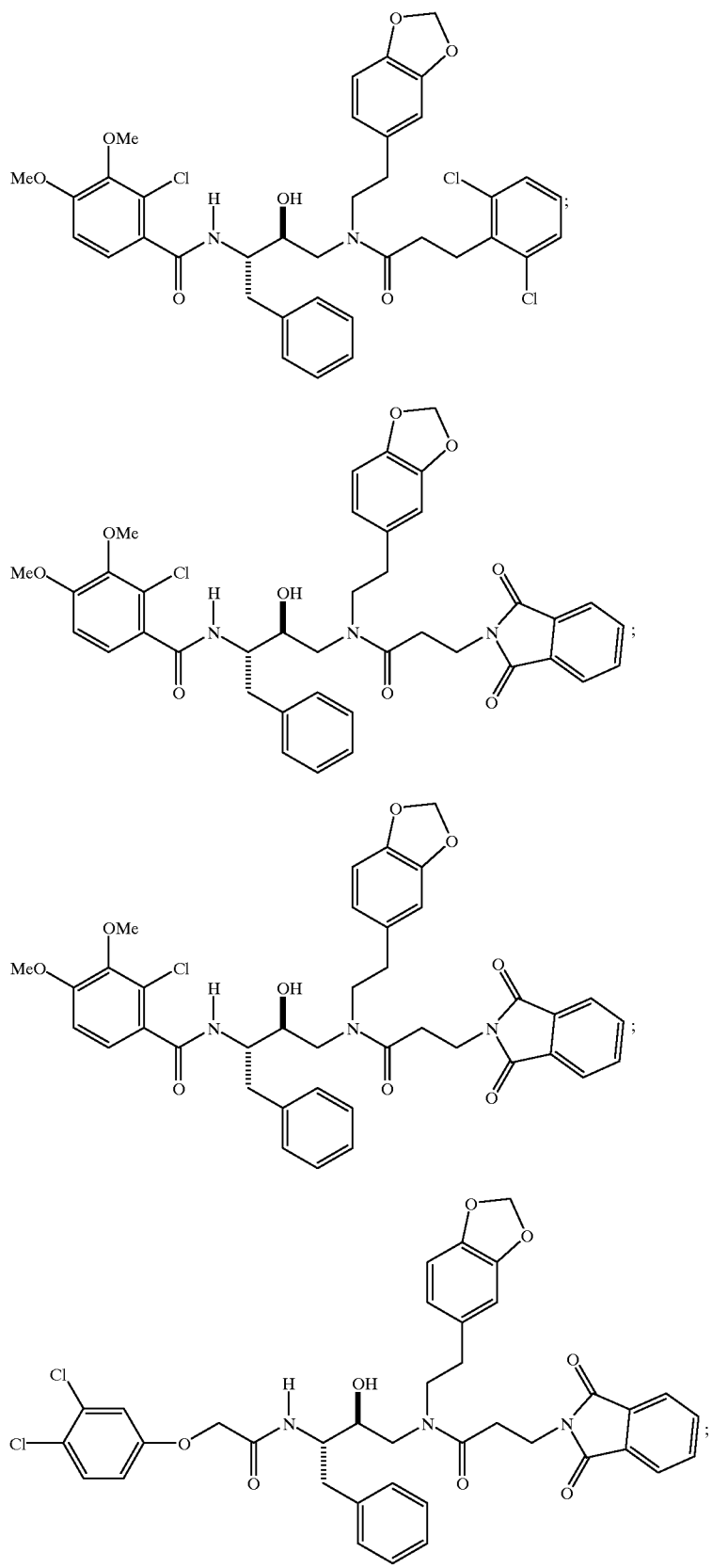

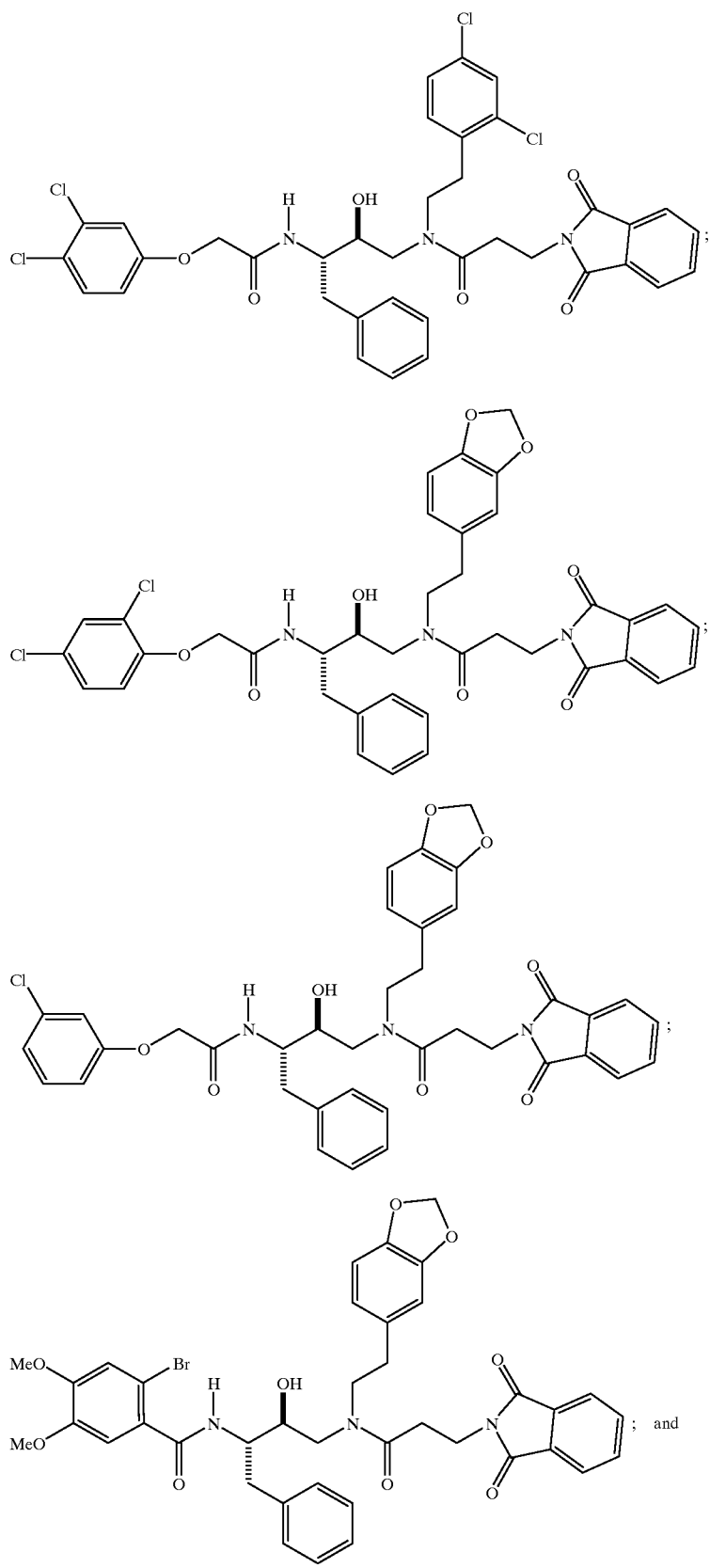

-continued
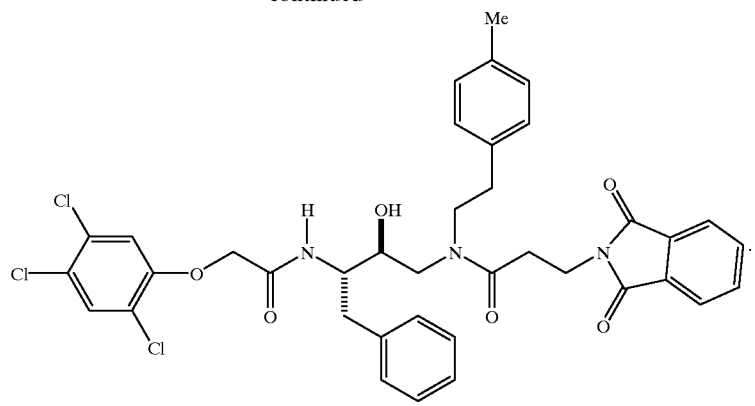
12. A compound in accordance with claim 1, wherein said compound is selected from group consisting of
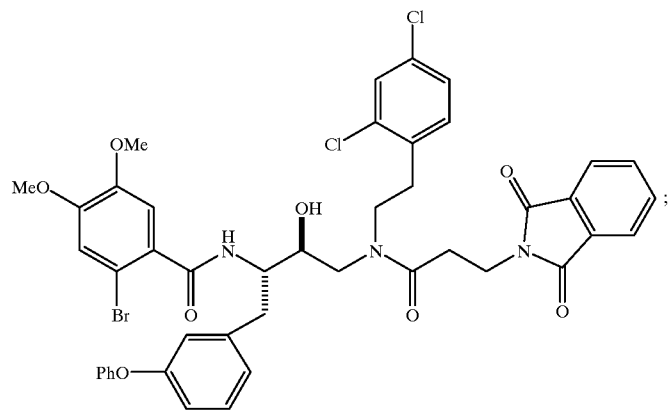
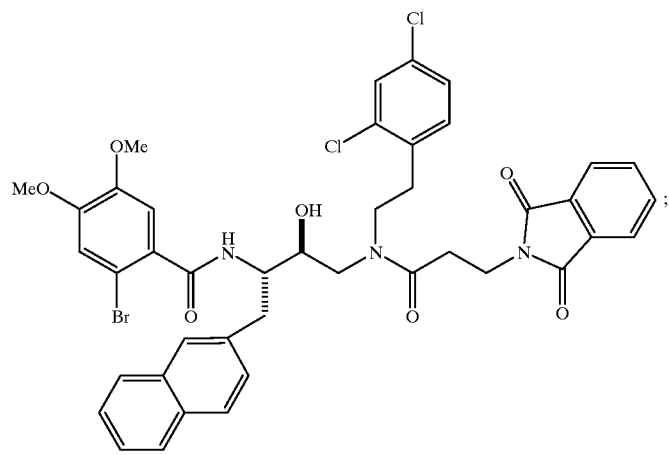

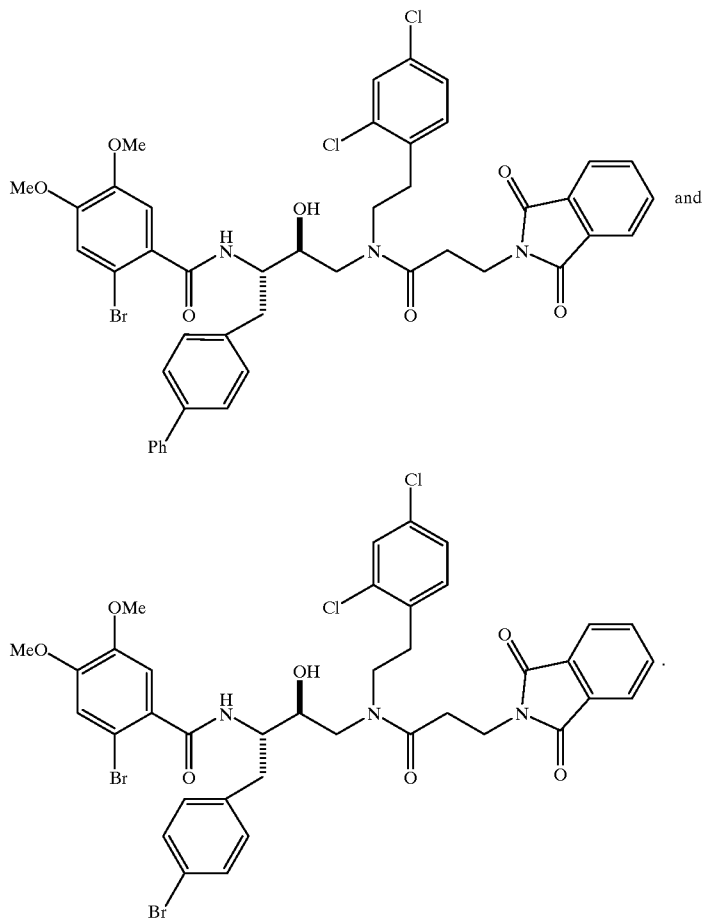

13. A method of inhibiting cathepsin D, said method comprising contacting cathepsin with a compound having the formula:

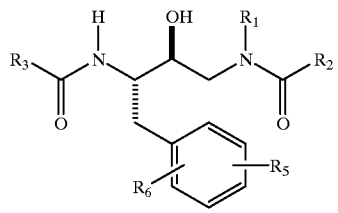

Formula I wherein:
- $R_1$, $R_2$ and $R_3$ alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl;
- $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R_5$ and $R_6$ and the carbons to which they are bound join to form an optionally substituted carbocyclic or heterocyclic fused ring system having a total of 9- or 10-ring atoms within said fused heterocyclic ring system, said heterocyclic fused ring system containing at least one member selected from the group consisting of a nitrogen atom, an oxygen atom and a sulfur atom.

14. The method in accordance with claim 13 wherein $R_1$ of said compound is a member selected from the group consisting of heteroarylalkyl and substituted arylalkyl.

15. The method in accordance with claim 13 wherein $R_1$ of said compound is a member selected from the group consisting of:

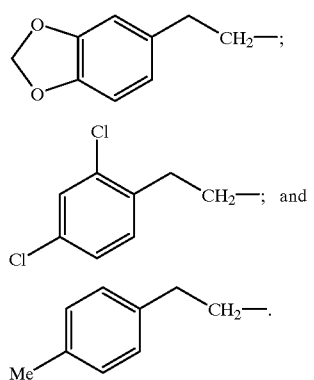

16. The method in accordance with claim 13 wherein $R_2$ of said compound is a member selected from the group consisting of heteroarylakyl, substituted arylalkyl and aryloxyalkyl.

17. The method in accordance with claim 13 wherein $R_2$ of said compound is a member selected from the group consisting of

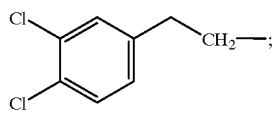

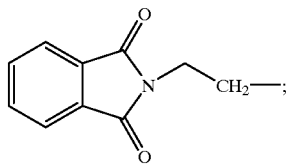

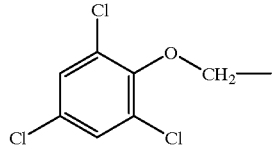

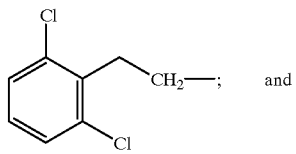 and

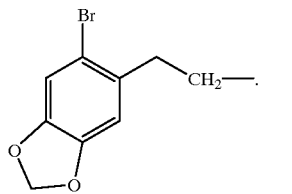

18. The method in accordance with claim 13 wherein $R_3$ of said compound is a member selected from the group consisting of substituted aryl, heteroarylalkyl and aryloxyalkyl.

19. The method in accordance with claim 13 wherein $R_3$ of said compound is a member selected from the group consisting of:

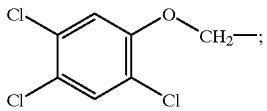

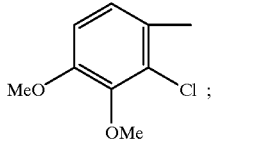

-continued

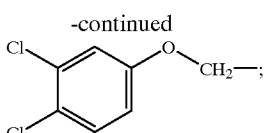

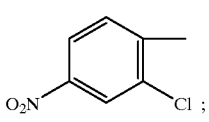

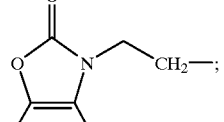

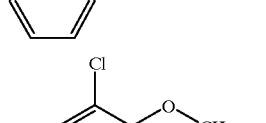

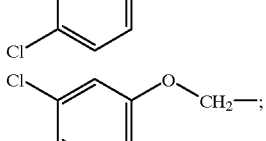

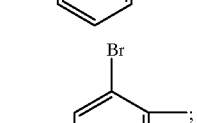

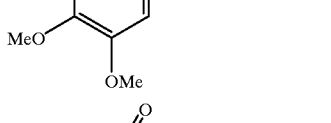 and

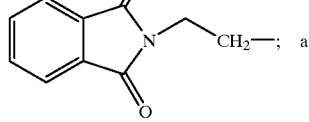

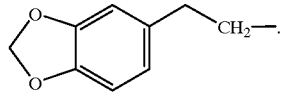

20. The method in accordance with claim 13, wherein $R_5$ and $R_6$ and the carbons to which they are bound join to form an optionally substituted napthalene ring.

21. The method in accordance with claim 13, wherein $R_5$ and $R_6$ are both hydrogen.

22. The method in accordance with claim 13, wherein $R_5$ is hydrogen and $R_6$ is a meta or para substituent selected from the group consisting of halogen, alkyl, substituted alkyl, aryl, substituted aryl, arylalkyl, substituted arylalkyl, aryloxyalkyl and substituted aryloxyalkyl.

23. A method of inhibiting cathepsin D in living cells, said method comprising contacting said cells with an effective amount of a compound having the formula:

Formula I

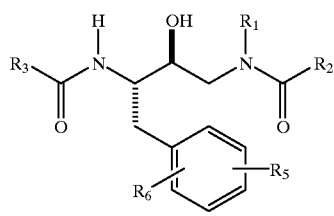

wherein:

$R_1$, $R_2$ and $R_3$ alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl;

$R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R_5$ and $R_6$ and the carbons to which they are bound join to form an optionally substituted carbocyclic or heterocyclic fused ring system having a total of 9- or 10-ring atoms within said fused heterocyclic ring system, said heterocyclic fused ring system containing at least one member selected from the group consisting of a nitrogen atom an oxygen atom and a sulfur atom.

24. The method in accordance with claim 23 wherein $R_1$ of said compound is a member selected from the group consisting of heteroarylalkyl and substituted arylalkyl.

25. The method in accordance with claim 23 wherein $R_1$ of said compound is a member selected from the group consisting of:

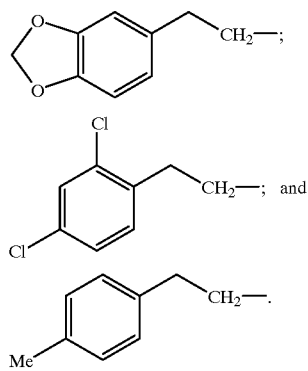

26. The method in accordance with claim 23 wherein $R_2$ of said compound is a member selected from the group consisting of heteroarylalkyl, substituted arylalkyl and aryloxyalkyl.

27. The method in accordance with claim 23 wherein $R_2$ of said compound is a member selected from the group consisting of

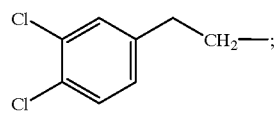

-continued

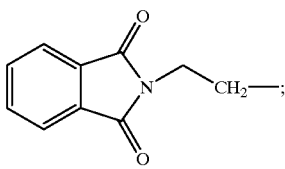

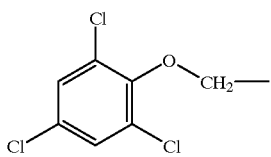

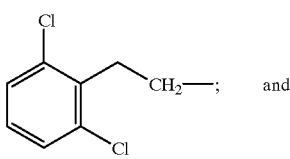

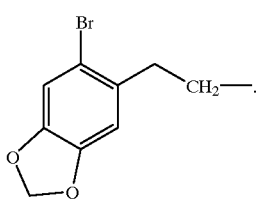

28. The method in accordance with claim 23 wherein $R_3$ of said compound is a member selected from the group consisting of substituted aryl, heteroarylalkyl and aryloxyalkyl.

29. The method in accordance with claim 23 wherein $R_5$ and $R_6$ and the carbons to which they are bound join to form an optionally substituted napthalene ring.

30. The method in accordance with claim 23 wherein $R_5$ and $R_6$ are both hydrogen.

31. The method in accordance with claim 23 wherein $R_5$ is hydrogen and $R_6$ is a meta or para substituent selected from the group consisting of halogen, alkyl, substituted alkyl, aryl, substituted aryl, arylalkyl, substituted arylalkyl, aryloxyalkyl and substituted aryloxyalkyl.

32. The method in accordance with claim 23 wherein $R_3$ of said compound is a member selected from the group consisting of:

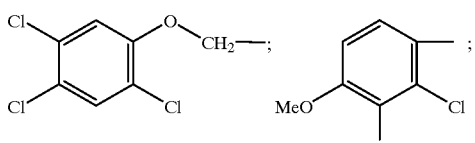

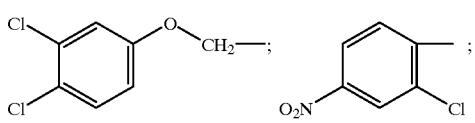

73
-continued
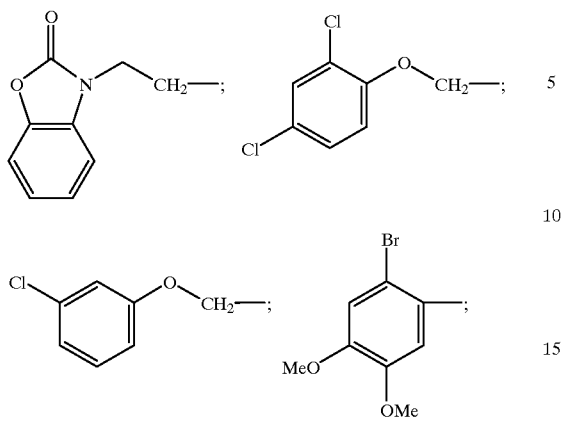
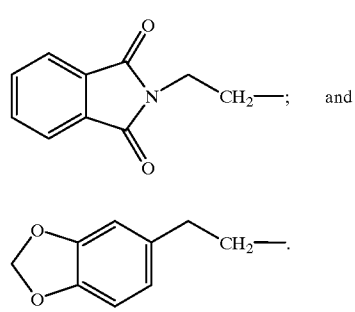
74
-continued
33. The method in accordance with claim 23 wherein said compound is selected from the group consisting of
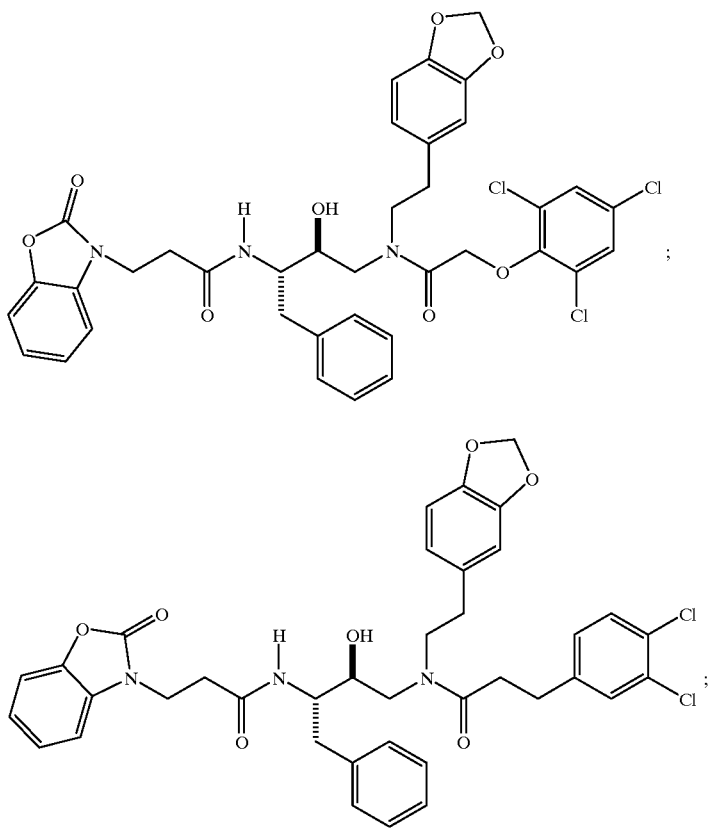

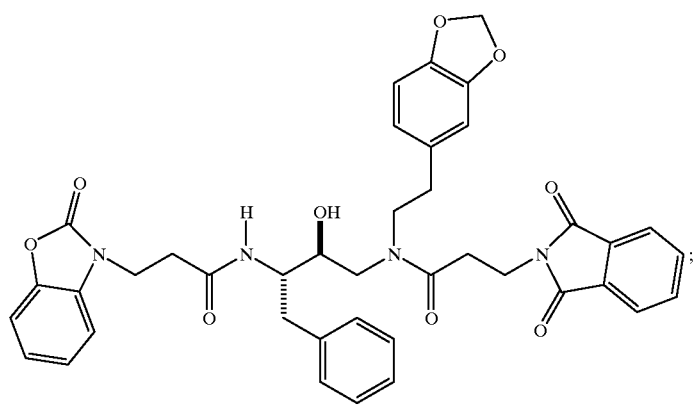
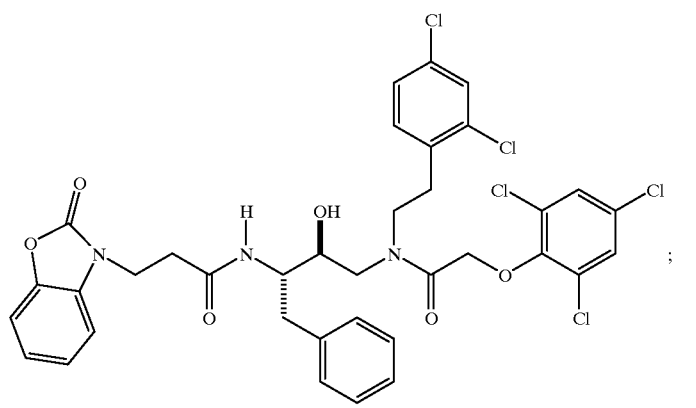
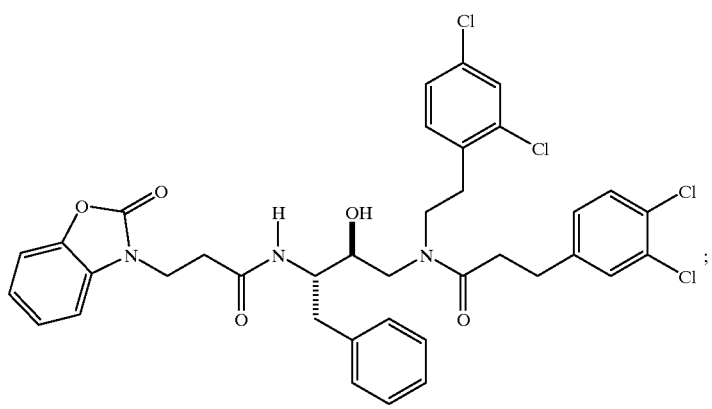
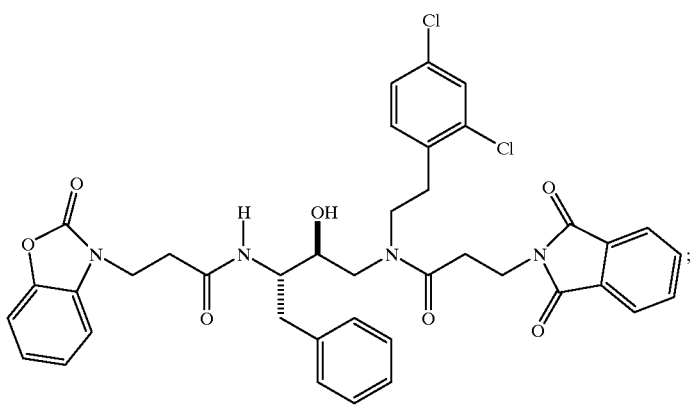

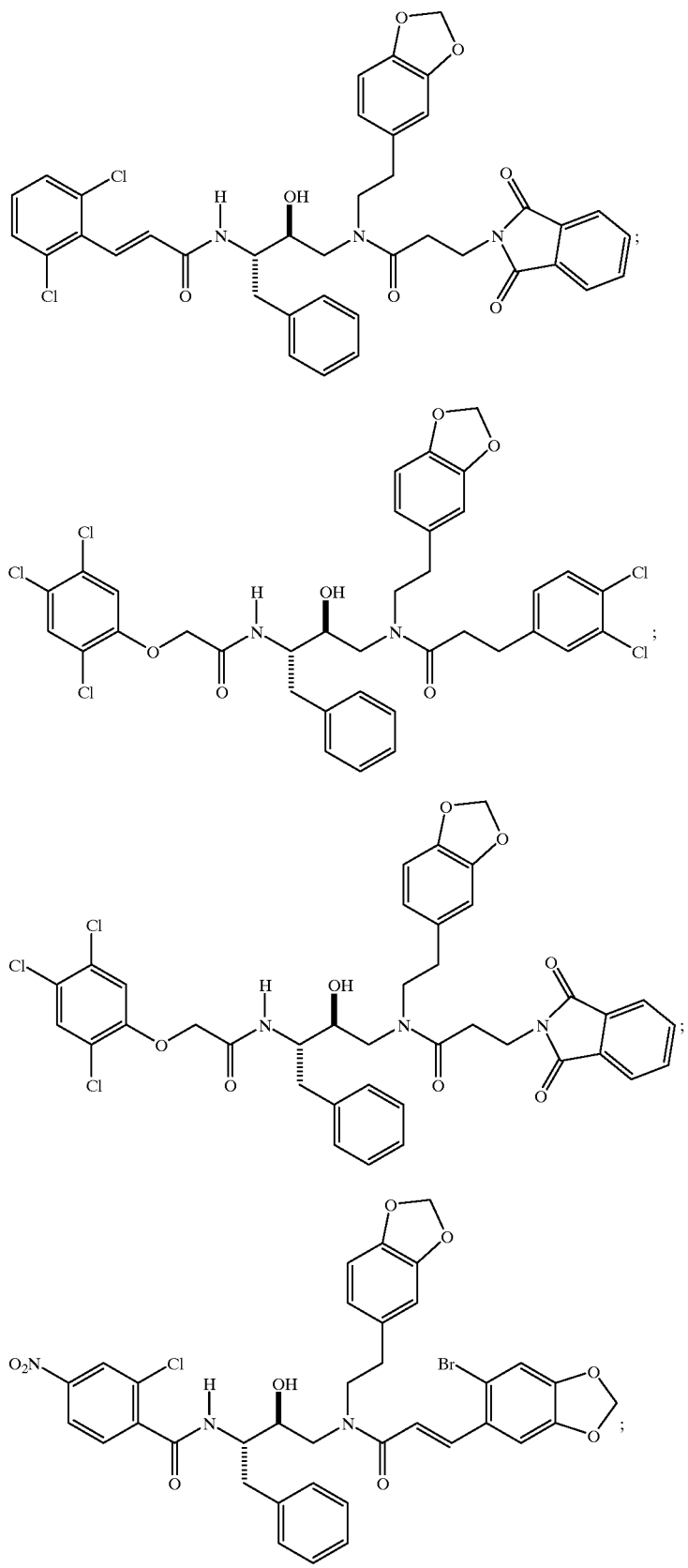

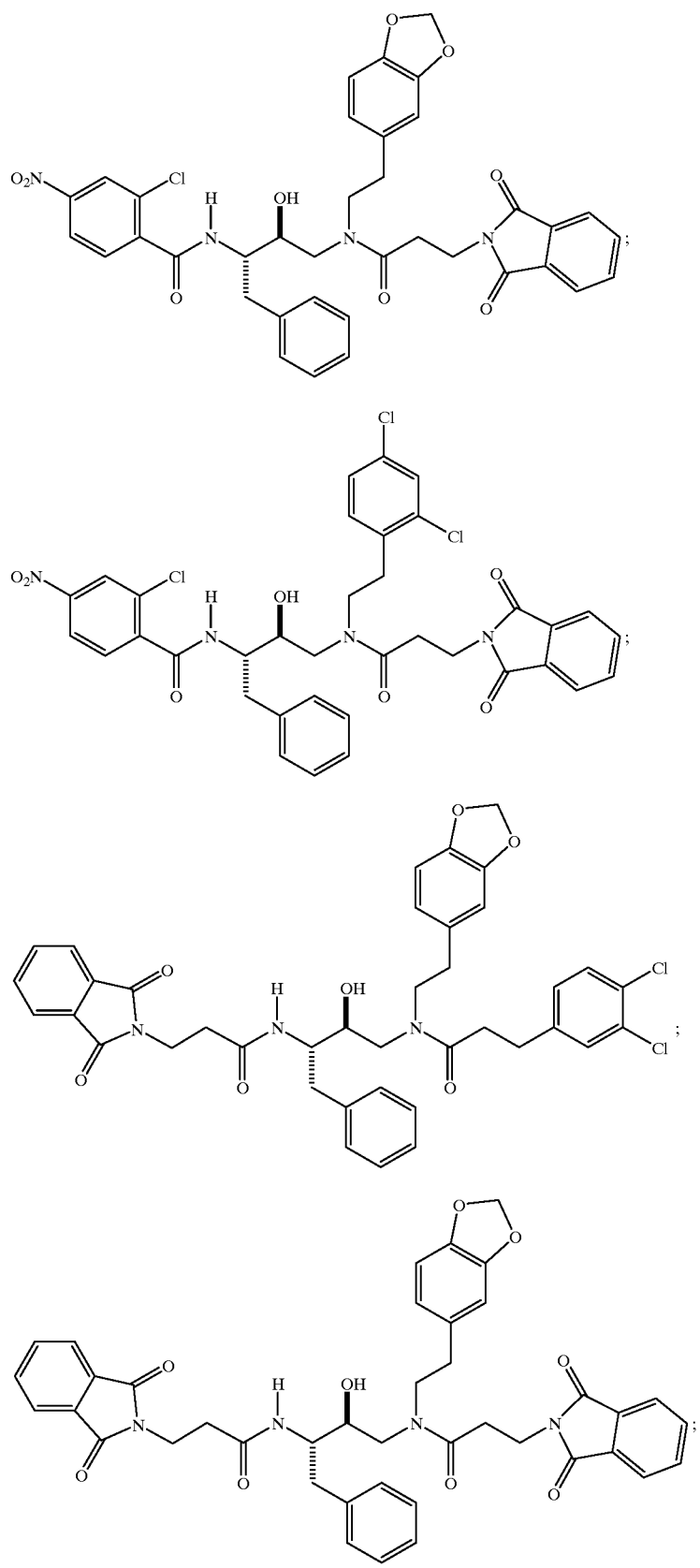

-continued
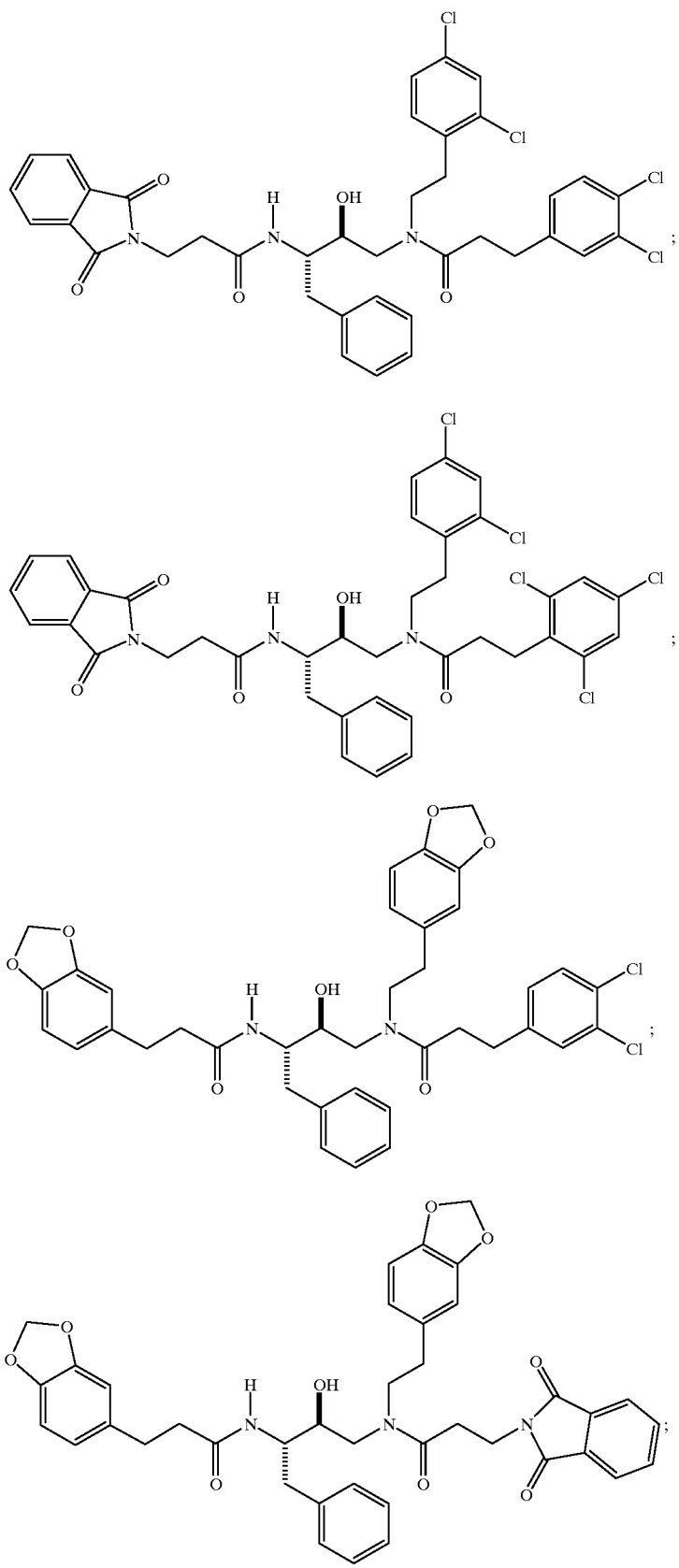

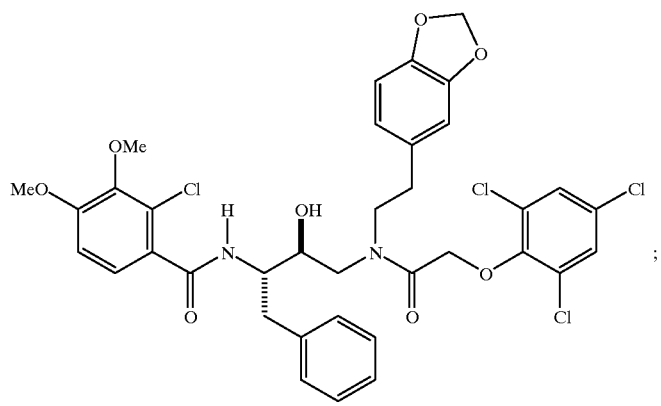
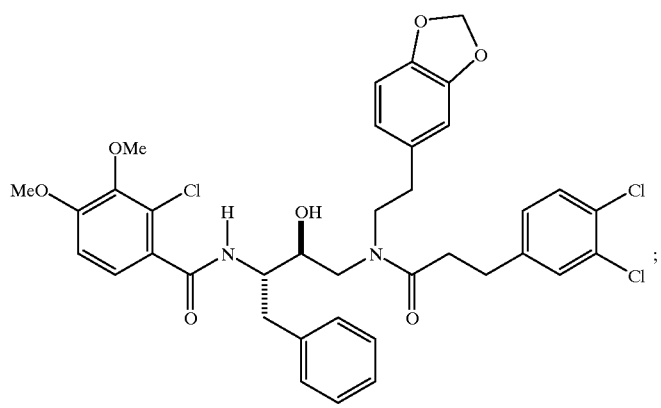
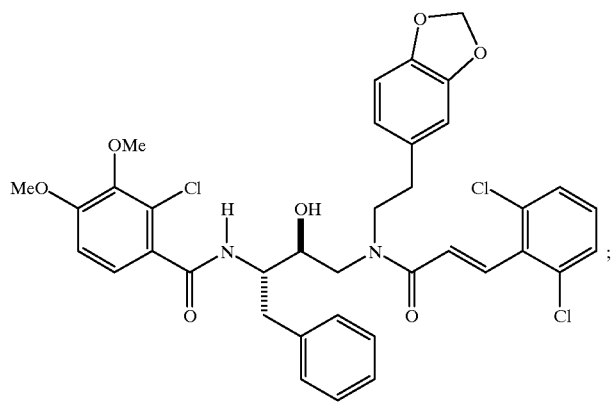
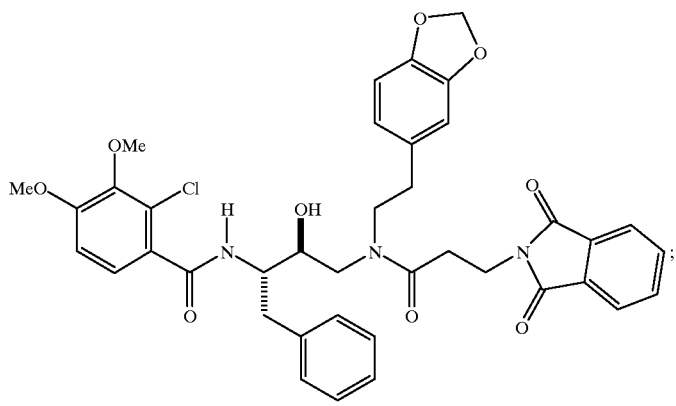

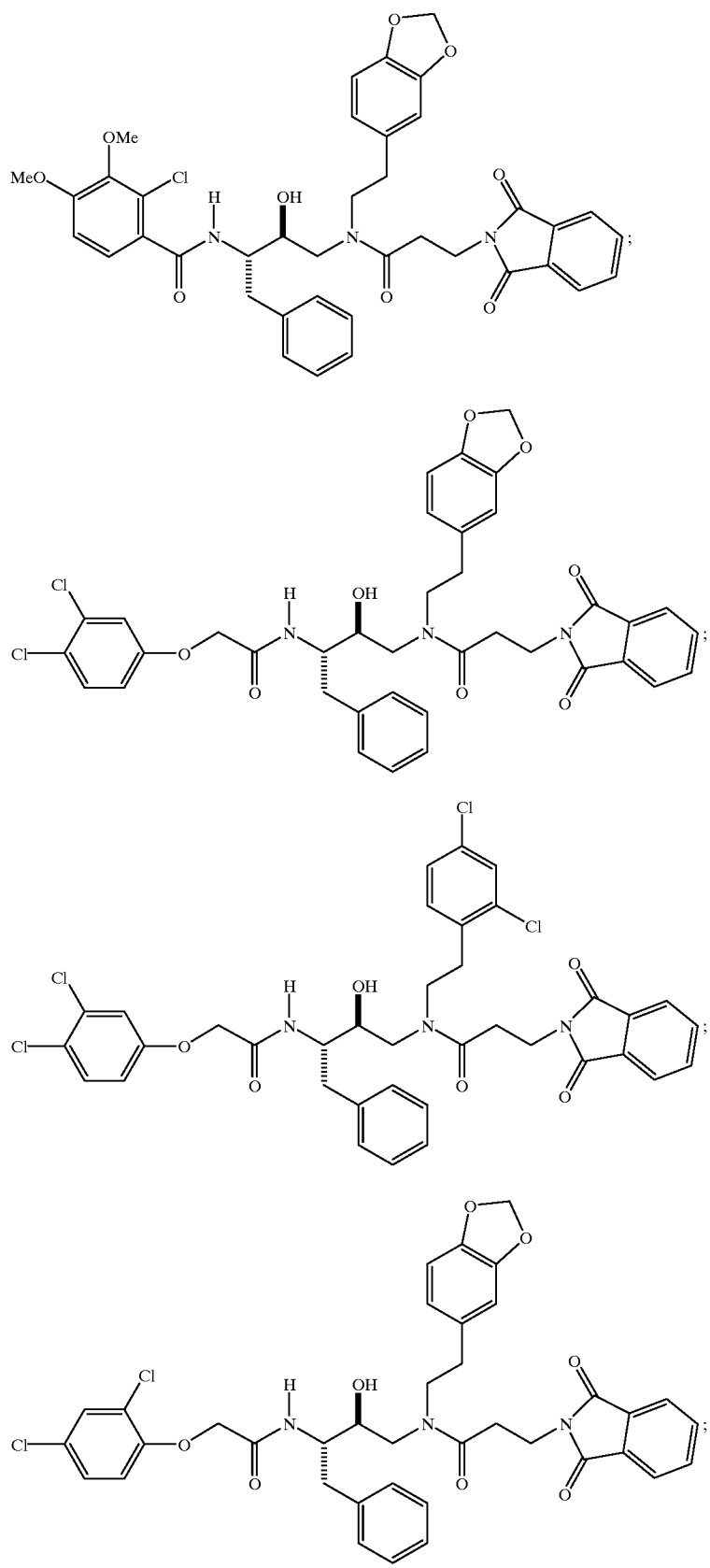

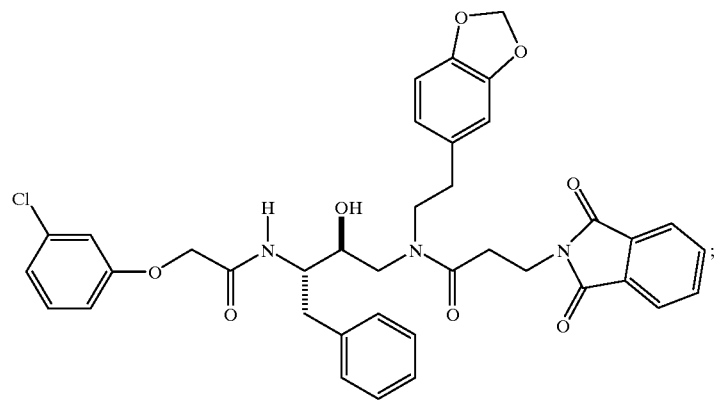
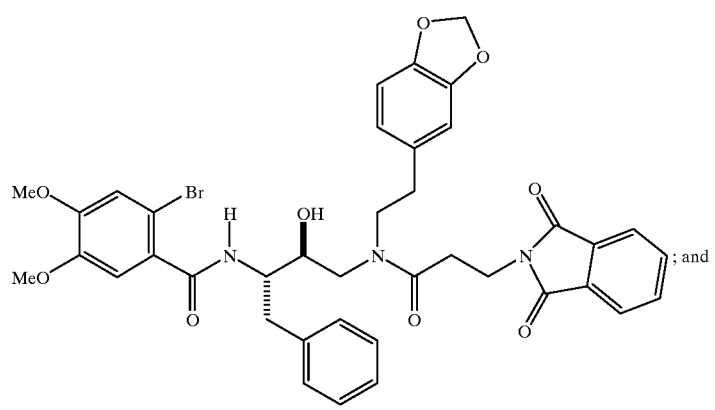
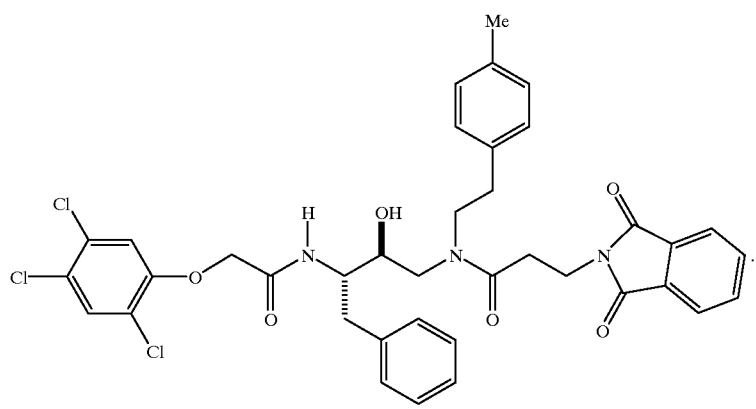

34. The method in accordance with claim 23 where said compound is selected from the group consisting of
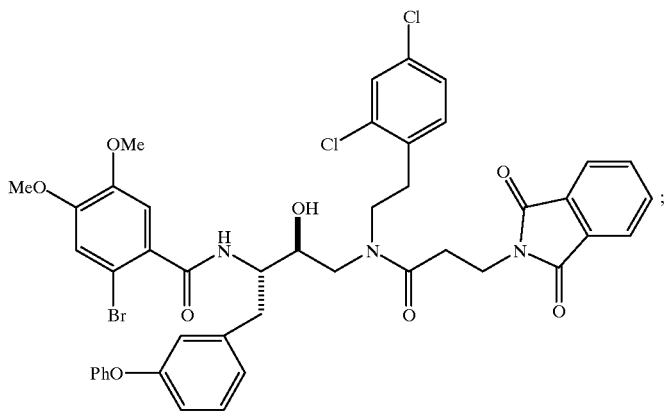
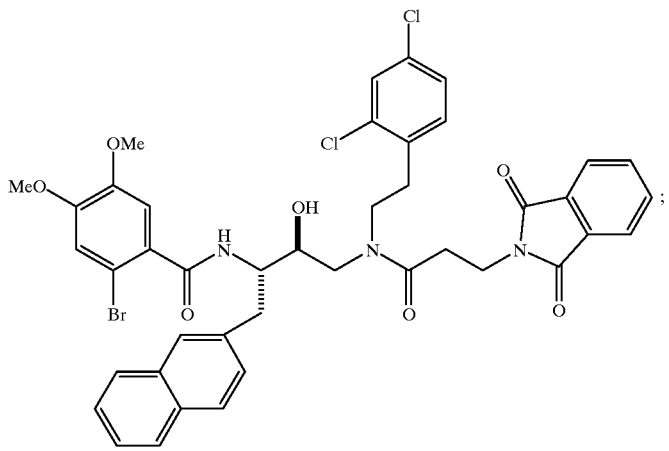
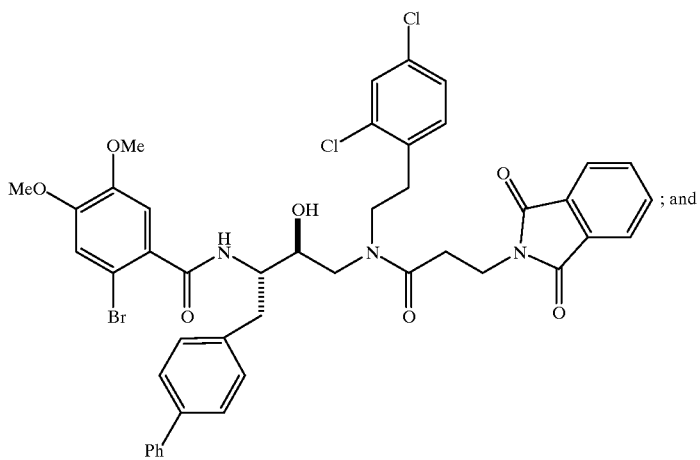

-continued

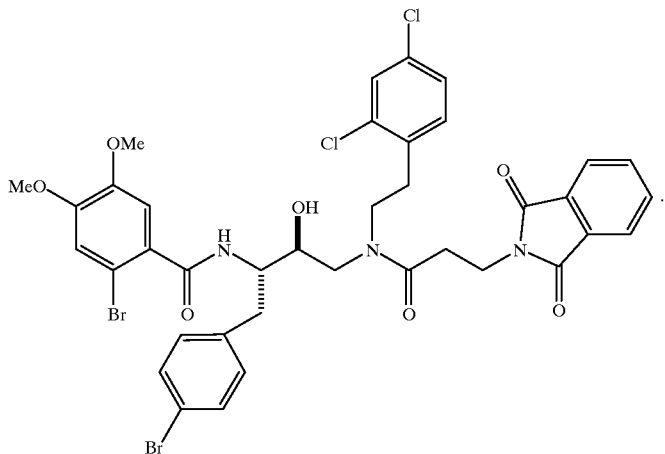

35. A pharmaceutical composition comprising a pharmaceutically acceptable excipient and a cathepsin D inhibitor having the formula:

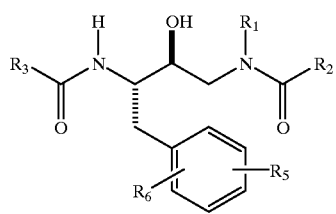

Formula I wherein:

$R_1$, $R_2$ and $R_3$ alkyl, substituted alkyl, aryl, substituted aryl, arylalkyl, substituted arylalkyl, aryloxyalkyl, substituted aryloxyalkyl, heteroaryl, substituted heteroaryl, heteroarylalkyl, substituted heteroarylalkyl, heterocycles, substituted heterocycles, heterocyclicalkyl and substituted heterocyclicalkyl; provided $R_2$ is not a radical which is a nitrogen-bonded cyclic α-amino acid or ester thereof, $R_5$ and $R_6$ are independently selected from the group consisting of hydrogen, halogen, alkyl, substituted alkyl, aryl, substituted aryl, arylalkyl, substituted arylalkyl, aryloxyalkyl and substituted aryloxyalkyl; or $R_5$ and $R_6$ and the carbons to which they are bound join to form an optionally substituted carbocyclic or heterocyclic fused ring system having a total of 9- or 10-ring atoms within said fused heterocyclic ring system, said heterocyclic fused ring system containing at least one member selected from the group consisting of a nitrogen atom, an oxygen atom and a sulfur atom.

* * * * *

UNITED STATES PATENT AND TRADEMARK OFFICE
CERTIFICATE OF CORRECTION

PATENT NO.    : 6,150,416
DATED         : November 21, 2000
INVENTOR(S)   : Ellen K. Kick et al.

It is certified that error appears in the above-identified patent and that said Letters Patent is hereby corrected as shown below:

<u>Column 48,</u>
Line 64, after "arylalkyl," insert -- phenyloxy, substituted phenyloxy, --.

<u>Column 67,</u>
Line 64, after "arylalkyl," insert -- phenyloxy, substituted phenyloxy, --.

<u>Column 71,</u>
Line 23, after "arylalkyl," insert -- phenyloxy, substituted phenyloxy, --.

<u>Column 92,</u>
Line 30, after "arylalkyl," insert -- phenyloxy, substituted phenyloxy, --.

Signed and Sealed this

Twenty-second Day of October, 2002

*Attest:*

*Attesting Officer*

JAMES E. ROGAN
*Director of the United States Patent and Trademark Office*